(12) United States Patent
Jain et al.

(10) Patent No.: US 10,285,634 B2
(45) Date of Patent: May 14, 2019

(54) EMOTION EVALUATION

(71) Applicant: Samsung Electronics Company, Ltd., Suwon, Gyeong gi-Do (KR)

(72) Inventors: Jawahar Jain, Los Altos, CA (US); Siddharth, San Diego, CA (US); Sajid Sadi, San Jose, CA (US); Pranav Mistry, Campbell, CA (US)

(73) Assignee: Samsung Electronics Company, Ltd., Suwon (KR)

( * ) Notice: Subject to any disclaimer, the term of this patent is extended or adjusted under 35 U.S.C. 154(b) by 157 days.

(21) Appl. No.: 15/202,407

(22) Filed: Jul. 5, 2016

(65) Prior Publication Data

US 2017/0007165 A1 Jan. 12, 2017

Related U.S. Application Data

(60) Provisional application No. 62/189,743, filed on Jul. 8, 2015.

(51) Int. Cl.
| | |
|---|---|
| *A61B 5/16* | (2006.01) |
| *A61B 5/00* | (2006.01) |
| *A61B 5/0478* | (2006.01) |
| *A61B 5/0205* | (2006.01) |
| *A61B 5/024* | (2006.01) |

(Continued)

(52) U.S. Cl.
CPC .......... *A61B 5/165* (2013.01); *A61B 5/0205* (2013.01); *A61B 5/02405* (2013.01); *A61B 5/0478* (2013.01); *A61B 5/40* (2013.01); *A61B 5/6803* (2013.01); *A61B 5/7278* (2013.01); *A61B 5/7445* (2013.01); *A61B 5/0402* (2013.01); *A61B 5/0476* (2013.01); *A61B 5/14551* (2013.01); *A61B 2560/0475* (2013.01)

(58) Field of Classification Search
CPC ..................................................... A61B 5/165
See application file for complete search history.

(56) References Cited

U.S. PATENT DOCUMENTS

| | | | |
|---|---|---|---|
| 6,021,346 | A | 2/2000 | Ryu |
| 6,292,688 | B1 | 9/2001 | Patton |

(Continued)

FOREIGN PATENT DOCUMENTS

| | | |
|---|---|---|
| KR | 20130032998 | 4/2013 |
| KR | 20140114588 | 9/2014 |

(Continued)

OTHER PUBLICATIONS

Eckberg, "Sympathovagal Balance: A Critical Appraisal," Circulation Nov. 4, 1997, vol. 96, Issue 9.*

(Continued)

*Primary Examiner* — Scott T Luan
(74) *Attorney, Agent, or Firm* — Baker Botts L.L.P.

(57) ABSTRACT

In one embodiment, one or more computer-readable non-transitory storage media embody software that is operable when executed to determine, based on cardiac-activity data, a shift in sympathovagal balance (SVB) during the period of time; obtain an emotional-state characteristic the emotional-state characteristic being based on brain-wave activity data; and determine, based on the SVB shift and the emotional-state characteristic, an estimate of an emotional state of the user during the period of time.

20 Claims, 11 Drawing Sheets

(51) Int. Cl.
  *A61B 5/0402* (2006.01)
  *A61B 5/0476* (2006.01)
  *A61B 5/1455* (2006.01)

(56) References Cited

U.S. PATENT DOCUMENTS

| 8,392,253 | B2 | 3/2013 | Pradeep |
| 8,396,744 | B2 | 3/2013 | Pradeep |
| 2003/0139654 | A1 | 7/2003 | Kim |
| 2005/0215916 | A1 | 9/2005 | Fadem |
| 2008/0221401 | A1 | 9/2008 | Derchak |
| 2009/0124869 | A1 | 5/2009 | Hu |
| 2013/0054090 | A1 | 2/2013 | Shin |
| 2015/0080698 | A1 | 3/2015 | Chiang |
| 2015/0099987 | A1 | 4/2015 | Bhatkar |
| 2015/0272465 | A1 | 10/2015 | Ishii |

FOREIGN PATENT DOCUMENTS

| KR | 20150010313 | 1/2015 |
| WO | WO 2005/015157 | 2/2005 |
| WO | WO 2010/038217 | 4/2010 |

OTHER PUBLICATIONS

Goldberger, "Sympathovagal balance: how should we measure it?," Am J Physiol. Apr. 1999;276(4 Pt 2):H1273-80.*
Heathers, "Sympathovagal balance from heart rate variability: an obituary," Exp Physiol. Apr. 2012;97(4):556.*
Emotiv Epoc, Brain Computer Interface and Scientific Contextual EEG, Emotiv Epoc & TestBench Specifications, Emotiv, 2014.
Christian J. Bell, Pradeep Shenoy, Rawichote Chalodhorn and Rajesh P N Rao, "Control of a humanoid robot by a noninvasive brain-computer interface in humans", Jorunal of Neural Engineering, 2008.
Karl LaFleur, Kaitlin Cassady, Alexander Doud, Kaleb Shades, Eitan Rogin and Bin He, "Quadcopter control in three-dimensional space using a noninvasive motor imagery-based brain—computer interface", Jorunal of Neural Engineering, 2013.
Jacob Webb, Zhen Gang Xiao, Katharina P. Aschenbrenner, Gil Herrnstadt, and Carlo Menon, "Towards a Portable Assistive Arm Exoskeleton for Stroke Patient Rehabilitation Controlled Through a Brain Computer Interface", Fourth IEEE RAS/EMBS International Conference on Biomedical Robotics and Biomechatronics, Roma, Italy, 2012.
Hidenori Boutani and Mieko Ohsuga, "Applicability of the "Emotiv EEG Neuroheadset" as a User-friendly Input Interface", 35th Annual International Conference of the IEEE EMBS, Japan, 2013.
Kusuma Mohanchandra, Vinay Krishnamurthy, et al., "Using Brain Waves as New Biometric Feature for Authenticating a Computer User in Real-Time", International Journal of Biometrics and Bioinformatics, vol. (7): Issue (1), 2013.
Mohamed Elgendi, Francois Vialatte, Martin Constable and Justin Dauwels, "Immersive Neurofeedback: a New Paradigm", International Conference on Neural Computation, 2011.
Mohamed Elgendi, Justin Dauwels, Brice Rebsamen, Rohit Shukla, et al., "From Auditory and Visual to Immersive Neurofeedback: Application to Diagnosis of Alzheimer's Disease", Springer, New York, in press, 2013.
International Search Report and Written Opinion for International Application No. PCT/KR2016/007425, dated Oct. 21, 2016.
Extended European Search Report for Application No. 16821683. 6-1132, dated May 23, 2018.

* cited by examiner

EMOTION EVALUATION

RELATED APPLICATION

This application claims the benefit, under 35 U.S.C. § 119(e), of U.S. Provisional Patent Application No. 62/189,743 filed 8 Jul. 2015, which is incorporated herein by reference.

TECHNICAL FIELD

This disclosure generally relates to wearable electronic devices.

BACKGROUND

An increasing interest in the evaluation human emotions may be seen in the behavioral, biological, and social sciences. Many phenomena, ranging from individual cognitive processing to social and collective behavior, may not be well understood without taking human emotions into account. Recently, there has been an interest in affective computing, which is the study and development of computing systems or devices that can recognize, interpret, process, and simulate human affects. In particular, the emotion of the user may be used as an input for subsequent operations by computing devices or systems.

DESCRIPTION OF EXAMPLE EMBODIMENTS

Figure 1:
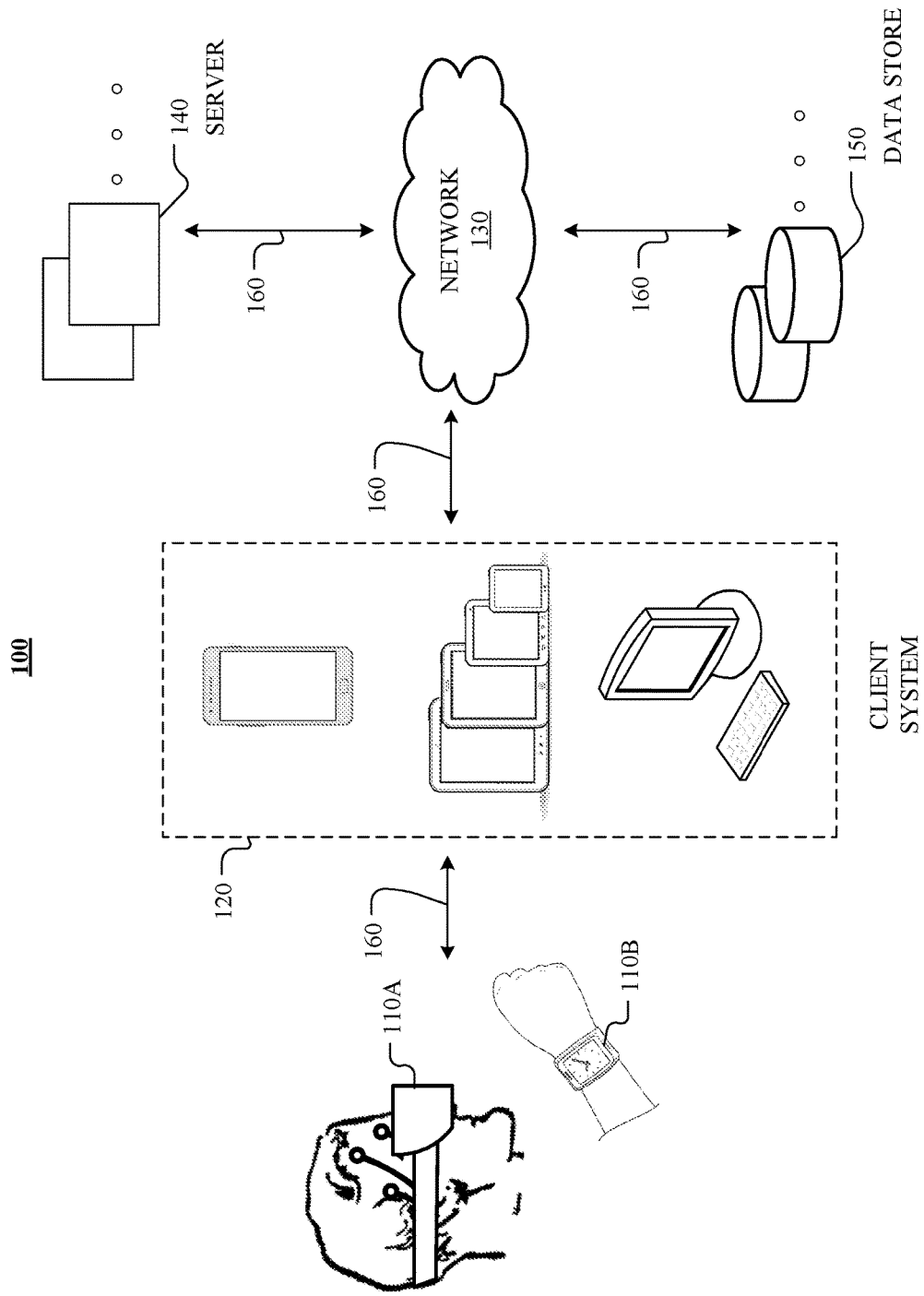
FIG. 1 illustrates an example network environment for particular embodiments of an optical detection system for internal body tissues and bone.

FIG. 1 illustrates an example network environment 100. Network environment 100 includes one or more wearable devices 110A-B, a client system 120, a network 130, one or more servers 140, and one or more data stores 150. Wearable devices 110A-B, client system 120, servers 140, and data stores 150 may be connected to each other by network 130 via links 160. Although FIG. 1 illustrates a particular arrangement of wearable devices 110A-B, client system 120, network 130, servers 140, and data stores 150, this disclosure contemplates any suitable arrangement of user 110, client system 120, network 130, servers 140, and data stores 150.

Network environment 100 includes one or more wearable devices 110A-B that may be connected to client system 120. In particular embodiments, one or more wearable devices 110A-B are a wearable electronic device (e.g., a device of client system 120) that can be worn on a portion of the user's body, such as an arm, wrist, finger, leg, ankle, toe, torso, neck, head, any other suitable portion of the body, or any combination thereof. In particular embodiments, one or more wearable devices 110A-B is configured to measure data from one or more systems of the human body. As an example and not by way of limitation, a first wearable device 110A may be configured to monitor electrical activity of the human brain and a second wearable device 110B may be configured to monitor the electrical activity of the human heart. Wearable devices 110A-B may be configured with integrated sensors, distributed sensors spanning multiple wearable devices, or any suitable configuration of sensors. In particular embodiments, one or more wearable devices 110A-B may include an augmented/virtual reality device (e.g., head mounted display (HMD)) or a user interface (UI).

In particular embodiments, wearable devices 110A-B may connect to client system 120 directly or via network 130, which may facilitate interaction between and/or transfer of data between wearable devices 110A-B and client system 120. Data (e.g., heart rate, brain wave activity, sleep time, emotional state, etc.) may be stored on wearable devices 110A-B, client systems 120, data stores 150, other suitable databases, or any combination thereof. In addition, the processing of the data and computations of particular algorithms (as discussed below) may be performed by wearable devices 110A-B, client system 120, servers 140, other suitable devices/systems, or any combination thereof. In particular embodiments, the processing of the data and computations of particular algorithms may be performed by accessing user data, frame of reference/baseline data, medical data, other relevant data, or any combination thereof, from data stores 150 via network 130.

As an example and not by way of limitation, two or more of client systems 120, servers 140, data stores 150, or any suitable combination thereof may be connected to each other directly (e.g., Ethernet or local area network (LAN) connection), bypassing network 130. As another example, two or more of client system 120, servers 140, and data stores 150 may be physically or logically co-located with each other in whole or in part. Moreover, although FIG. 1 illustrates a particular number and configuration of wearable devices 110A-B, client system 120, network 130, servers 140, and data stores 150, this disclosure contemplates any suitable number or configuration of wearable devices 110A-B, client system 120, network 130, servers 140, and data stores 150. As an example and not by way of limitation, network environment 100 may include multiple wearable devices 110A-B, client systems 120, networks 130, servers 140, and data stores 150.

In particular embodiments, client system 120 may be any suitable computing device, such as, for example, a mobile computing device, a smartphone, a cellular telephone, a tablet computer, a laptop computer, a personal computer, or any combination thereof. User may interact with one or more of these devices. In addition, these devices may communicate with each other via network 130, directly (e.g., by non-network connections), by any other suitable methods, or any combination thereof. As an example and not by way of limitation, client system 120 may communicate with network 130 via a wireless communications protocol, such as Wi-Fi or BLUETOOTH. In particular embodiments, network 130 may be any suitable network. As an example and not by way of limitation, one or more portions of network 130 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 130 may include one or more networks.

In particular embodiments, links 160 may connect client system 120, servers 140, and data stores 150 to network 130 or to each other. This disclosure contemplates any suitable links 160. In particular embodiments, one or more links 160 include one or more wireline (such as for example Digital Subscriber Line (DSL) or Data Over Cable Service Interface Specification (DOC SIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 160 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 160, or a combination of two or more such links 160. Links 160 need not necessarily be the same throughout network environment 100, such that one or more first links 160 may differ in one or more respects from one or more second links 160.

In particular embodiments, servers 140 may be any suitable servers. Each server 140 may be a unitary server or a distributed server spanning multiple computers or multiple datacenters. Servers 140 may be of various types, such as, for example and without limitation, web server, file server, application server, exchange server, database server, proxy server, another server suitable for performing functions or processes described herein, or any combination thereof. In particular embodiments, each server 140 may include hardware, software, or embedded logic components or a combination of two or more such components for carrying out the appropriate functionalities implemented or supported by server 140.

In particular embodiments, data stores 150 may be any suitable data stores. Data stores 150 may be used to store various types of information. In particular embodiments, the information stored in data stores 150 may be organized according to specific data structures. In particular embodiments, each data store 150 may be a relational, columnar, correlation, or other suitable database. Data store 150 may include networked storage such as cloud storage or other network accessible storage. Additionally or alternatively, data store 150 may include local storage within or directly attached to any of the devices of client system 120, such as solid state drives (SSDs) or hard-disk drives (HDDs).

In particular embodiments, data store 150 may store various data structures relevant to an optical detection device and the processing of data collected by the optical detection device. As an example and not by way of limitation, data store 150 may store a data structure corresponding to bio-sensing measurements (e.g., measurements of heart rate (HR), heart-rate variation (HRV), data derived from HR or HRV (e.g., sympathovagal balance (SVB)), or "brainwave" patterns (e.g., electroencephalogram (EEG) data). As another example and not by way of limitation, data store 150 may store a data structure corresponding to features data and features vectors determined based on a features evaluation process for emotion evaluation. Although this disclosure describes or illustrates particular types of components and uses of these component of network environment 100, this disclosure contemplates any suitable types of components, any suitable network topology (e.g., including a standalone-device topology), and any suitable uses for these components of network environment 100.

As described above, the automated evaluation of human emotions is useful in the behavioral, biological, and social applications, among others. Particular embodiments discussed below describe the evaluation of human emotions in the context of mobile monitoring use in personalized entertainment experiences. In mobile monitoring, use of wearable devices 110A-B with sensors can facilitate real-time evaluation of human emotions. In particular embodiments, human emotions are evaluated by measuring the activities/arousal of the autonomic nervous system (ANS), where changes in arousal are indicators for various emotions. For example, the arousal of ANS leads to changes in the physiology that may be measured via changes in heart rate, skin conductance, blood pressure, respiration, brain wave patterns via an EEG, other relevant metrics, or any combination thereof. Particular embodiments described below describe monitoring and measurement of pathophysiological interplays of the nervous and cardiovascular systems.

The changes in the human emotions can be measured, in part, by changes in EEG values or brain-wave activity over different locations of the brain. For instance, the brain responds to different stimuli and conditions differently and hence different human emotions have a differentiable mark on the brain activity. In particular embodiments, wearable device 110A may include sensors that are configured to measure electrical "brain-wave" activity (e.g., EEG).

Wearable device 110A can include, as stated, a number of EEG sensors (e.g., 14 sensors) positioned in a pattern such that the sensors measure particular regions of a user's head. In one example aspect, among others, the total number of EEG sensors being used and the positioning of each sensor on the head can affect the accuracy, resolution, and/or reliability of the extraction of brain-wave features. During sensor data processing, one or more of the devices 110A, 110B, 120, 140 can link the sensor data from each of the EEG sensor to a predetermined region of the brain. The brain-wave measurements are processed, as described in greater detail below, to determine trends (e.g., to determine whether EEG excitement or arousal is increasing or decreasing). Although this disclosure illustrates and describes a particular type of wearable device configured to measure brain-wave activity having a particular configuration of sensors, this disclosure contemplates any suitable types of device having any suitable configuration of sensors for measuring brain-wave activity.

In particular embodiments, brain-wave activity is measured in pre-defined frequency bands. The pre-defined frequency bands can include, for example, Alpha (7-13 Hz); Beta 1 or Low Beta waves (~13-20 Hz); and Beta 2 or Beta waves (~20-30 Hz). Alpha wave features originate from the posterior regions of the brain on both sides and are higher in amplitude on the dominant side. Beta wave features originate from both sides of the brain in a symmetrical distribution and are most evident frontally. Beta wave activity is closely linked to motor behavior and is generally attenuated during active movements. The Gamma frequency band is ignored in example embodiments due to a high level of noise. Energy levels of the pre-defined spectral bands of the EEG is used as features and the energy levels is calculated for data measured over a pre-determined time period (e.g., 1 second) for each of the sensors of wearable device 110A.

An example feature, for instance, is an energy level that is greater than a predefined threshold and, in some embodiments, for a duration greater than a predetermined time. This type of feature can be indicative of a type of brain-wave activity corresponding to, e.g., the corresponding frequency band and/or region of the brain. Other example features are the symmetries or asymmetries of measured brain-wave activity with respect to the regions of the user's brain.

In particular embodiments, the features (e.g., such as energy in that band or power spectral density (PSD)) of frequency bins corresponding to the different spectral bands are calculated by converting the discrete-time signal from the sensors of wearable device 110A into the frequency domain using the fast-Fourier transform (FFT) algorithm. In particular embodiments, the value of the features are normalized to a value in the range between 0 and 1. The total number of features captured by the sensors of wearable device 110A may be very large. Some of the captured features may not be used for emotion evaluation, hence, the total number of features may be reduced based on heuristics. In particular embodiments, feature reduction is performed using principal component analysis (PCA) algorithm that projects the data into a multi-dimensional space such that this projection corresponds to best representation of the original data without significant loss of information.

As described above, wearable device 110B may include one or more sensors configured to measure cardiovascular data. There are a number of types of sensors that can be deployed. In particular embodiments, wearable device 110B may measure cardiovascular activity through photoplethysmogram (PPG) that illuminates the underlying skin and determines cardiovascular activity based on changes in light absorption. As an example and not by way of limitation, PPG measures a change in volume caused by the pressure pulse that is detected by illuminating the skin with the light from a light-emitting diode (LED) and then measuring the amount of light either transmitted or reflected to a photodiode of wearable device 110B. Additionally or alternatively, wearable device 110B may measure cardiovascular activity through electrocariography (ECG) that measures electrical activity of the heart using electrodes placed on the skin. As an example and not by way of limitation, wearable device 110B may be a chest strap with one or more electrodes that are configured to measure cardiac electrical activity. Although this disclosure illustrates and describes a particular type of wearable device configured to measure cardiovascular activity having a particular configuration of sensors, this disclosure contemplates any suitable types of device having any suitable configuration of sensors for measuring cardiovascular activity.

Bio-sensing measurements, such as PPG data, may be noisy and bio-signals derived from these measurements may be noise sensitive. As an example and not by way of limitation, sources of noise include motion artifacts, erratic and/or lose body-senor contacts, ambient disturbances, or other relevant noise. Specifically, noise increases the variability of collected signal data, which may erroneously increase the perceived variability in the HRV computation, which may then erroneously affect the SVB output. As an example and not by way of limitation, noise is highly prominent in PPG signals, which is a sensitive bio-signal with low tolerance for anything less than ideal collection and analysis methods. The particular embodiments discussed below pertain to monitoring and analyzing suitable bio-signals relevant to health and/or wellness with noisy measurements. Health measurements is calculated from data captured by a bio-sensing device (e.g., one or more wearable devices 110A-B, a mobile device (e.g., a smart phone.), a specialized monitoring device (e.g., a medical device, etc.), other suitable devices, or any combination thereof (e.g., as described above with regard to FIG. 1). As an example and not by way of limitation, health measurements may include stress, heart rate, sleep, emotional state, other relevant measurements, or any combination thereof. For example, the data may correspond to an EEG signal, PPG signal, ECG signal, a bio-impedance signal, arterial blood pressure (BP signal), other suitable signals, or any combination thereof. As described above, a PPG signal is used to calculate HRV, which in turn is used to calculate SVB. However, noise in the PPG signal may cause an increase in variability in the HRV calculation that in turn results in an erroneous SVB measurements. Embodiments described below describe correcting errors resulting from the noise in a PPG signal or EEG signal.

In particular embodiments, correcting a noisy signal (e.g., a PPG signal or EEG signal) may be based on the observation that jitters or signal distortions can be local to peak or trough or zero-crossings. For signal distortions near maxima, minima, or zero-crossings of the signal, the noise is estimated by computing an expected signal profile, and then blend a constructed signal determined based on the expected signal profile with the raw signal. In the case of high signal distortions, the relevant portion of the signal may be completely thrown out and replaced with a constructed signal that is determined based on the expected signal profile. The constructed signal provides a good PPG signal or EEG signal with low noise for use or analysis. Stitching and/or replacing noisy signals may be done in real-time in order to output a relatively noise-free signal.

Figure 2A:
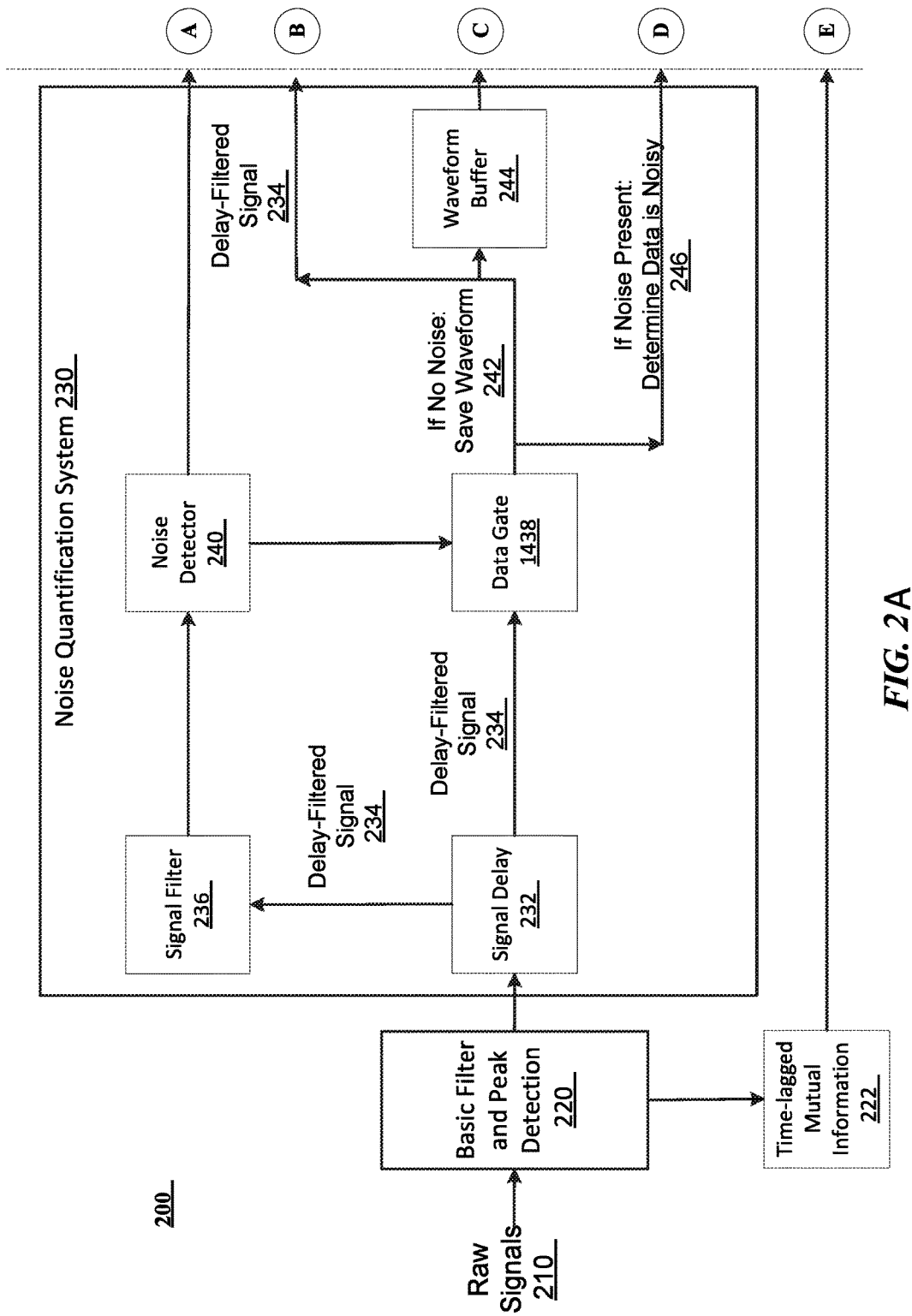
FIGS. 2A-2C illustrate a noise correction system for noise prediction and signal stitching or replacement.
Figure 2B:
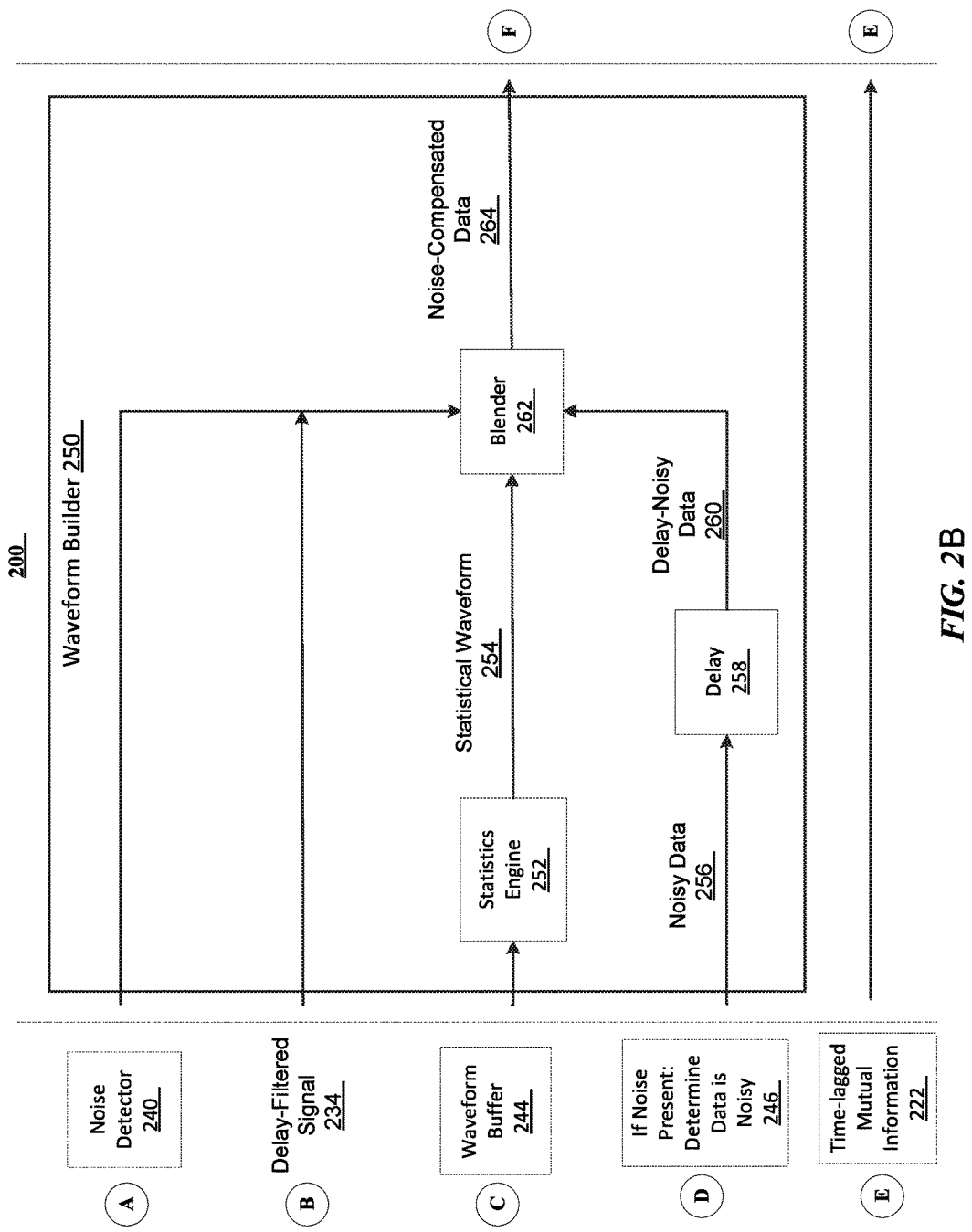
Figure 2C:
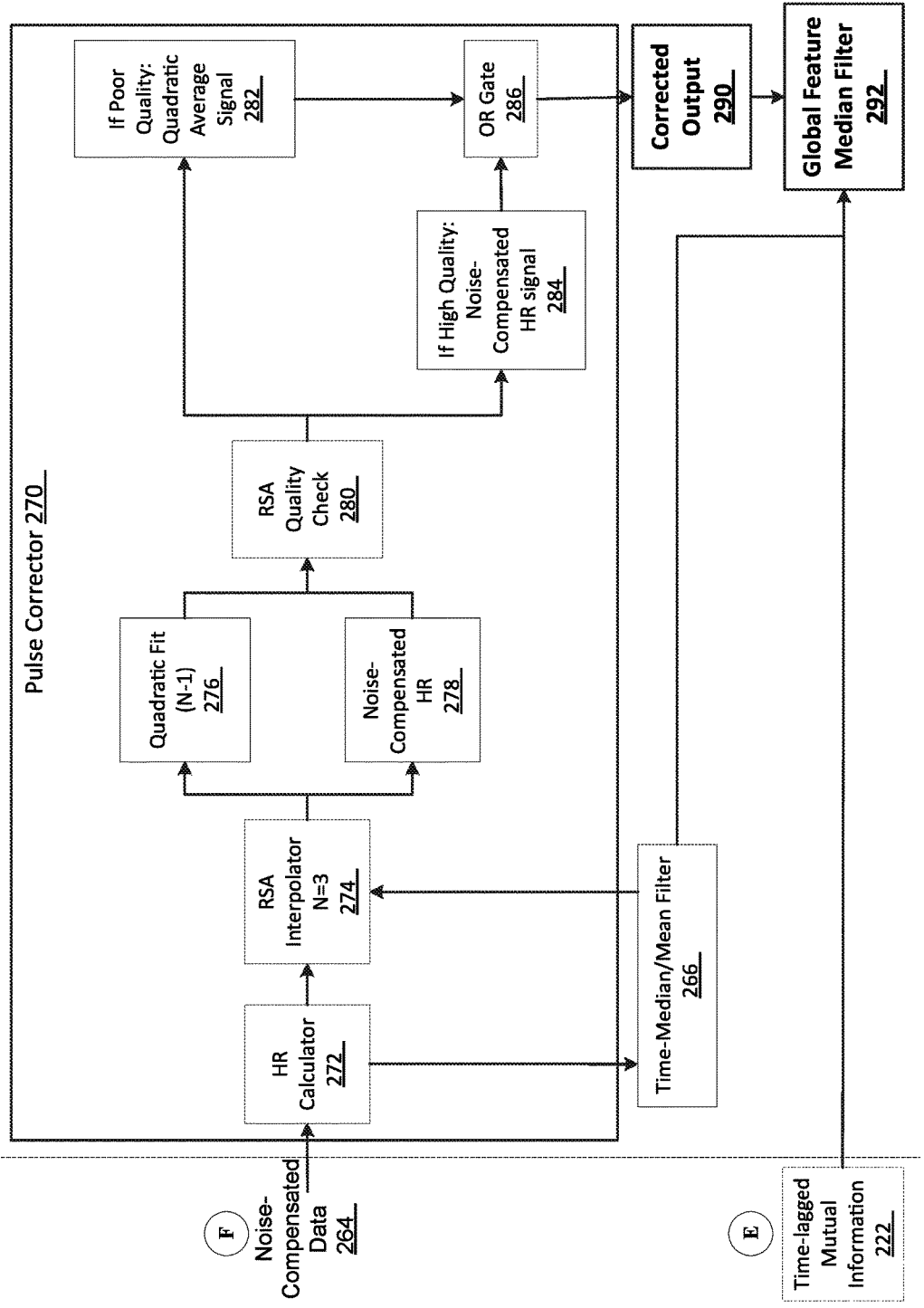

FIGS. 2A-2C illustrate a noise correction system 200 for noise prediction and signal stitching or replacement. As described below, a relationship between signal noise and estimated error is determined. In particular embodiments, this relationship may be implemented as a computed relationship (e.g., an equation) or as a look-up table. Accordingly, based on a computed noise level, the error-noise curve can be used to determine an estimated error. The error can be given in term of either HRV or SVB computation, and the adjustment can be applied to the corresponded computation.

Noise correction system 200, which may be executed on wearable devices 110A-B or client system 120, may initially receive an input of raw signals 210. As described above, raw signals 210 may be received from the sensor (or sensor interface) are processed through basic filtering and peak detection 220. As an example and not by way of limitation, the raw signals 210 may be processed through basic filtering to remove a portion of noise (e.g., any blocks of the raw signals with a frequency greater than 15 Hz). In addition, the raw signals 210 may be processed so that peak detection may be conducted on the signal, and this information may be stored for later use (e.g., to determine whether a signal is noisy or not).

The filtered raw signal is sent to noise quantification system 230. In particular embodiments, noise quantification system 230 may include a signal delay 232, a signal filter 236, a data gate 238, a noise detector 240, and a waveform buffer 246. In particular embodiments, the filtered raw signal is sent to signal delay 232, where the delay-filtered signal 234 is sent to both signal filter 236 and data gate 238. In particular embodiments, signal delay 232 may store and maintain the filtered raw signal for a predetermined period of time before passing the delay-filtered signal 234 to data gate 238 so that the delay-filtered signal 234 sent to signal filter 236 may be analyzed by noise detector 240 to determine whether noise is present (e.g., so that the noise may be detected and handled in approximately real-time). In determining whether noise is present, noise detector 240 may compute relative pulse width and pulse amplitudes (e.g., between a first pulse and one or more second subsequent pulses) and compare with physiologically acceptable deviations, and metric changes greater than the physiologically acceptable deviations may be considered to be noise. As an example and not by way of limitation, for a PPG waveform, signal delay 232 may maintain (e.g., "delay") the filtered raw signal for a period of about 100 samples, which corresponds to about a single pulse of a heartbeat. This way, if it is determined that the filtered raw signal contains noise, then noise correction system 200 may go back to the beginning of the single pulse (e.g., located somewhere in the 100 samples) and correct the filtered raw signal before the noise occurs. In particular embodiments, for the PPG waveform signal, the beginning of the single waveform may be a peak (e.g., where the single pulse is determined based on a pulse-peak to the next pulse-peak), a trough (e.g., where the single pulse is determined based on a trough to the next trough), a zero-crossing (e.g., where the single pulse is determined based on a zero-crossing to the next zero-crossing), other relevant waveform feature, or any combination thereof. Particular waveform features and advantages of specific waveform features are discussed in more detail below.

Once noise detector 240 determines whether or not noise is present in the delay-filtered signal 234, this determination is sent to data gate 238 in addition to being sent to a blender 262. If it is determined that there is no noise (e.g., step 242), then the delay-filtered signal 234 is saved and inputted into a waveform buffer 244, while also being sent to blender 262 (discussed below). In particular embodiments, waveform buffer 244 (e.g., a memory buffer) may store only a predetermined amount of data. As an example and not by way of limitation, for the PPG waveform signal, waveform buffer 244 may store only data corresponding to three pulses of heartbeats (e.g., N=3). Waveform buffer 244 may be configured to store a small number of pulses such that noisy signals (e.g., pulse signals with large deviations in one or more features as compared with one or more previous pulse signals) may be determined to noisy in comparison with previous signals but at the same time allowing for gradual changes in the signal. In addition, when waveform buffer 244 starts with nothing in the buffer (e.g., no PPG waveforms stored), the initial determination will be that the delay-filtered signal does not contain noise such that at least three PPG pulses may be stored before analyzing the waveform of a present PPG pulse with the waveform of a previous PPG pulse. Then, after there are three non-noisy PPG waveforms stored in waveform buffer 244, each additional PPG waveform that is determined to not be noisy is saved to waveform buffer 244 while an old PPG waveform (e.g., the PPG waveform from four pulses ago) will be removed. This way, waveform buffer 244 may always maintain the last three PPG waveforms corresponding to the last three pulses.

In particular embodiments, the number of pulses stored in waveform buffer 244 may be small enough to allow for meaningful comparison and also may be large enough to average out inter-pulse deviations and noise. Herein reference to the term R may refer to a point corresponding to the peak of the QRS complex of the PPG waveform or the largest pressure gradient at the aorta, and reference to the term RR interval refers to the interval between successive R's. As an example and not by way of limitation, three pulses of heartbeats is stored in waveform buffer 244 due to the phenomenon of respiratory-sinus arrhythmia (RSA), which is heart-rate variability in synchrony with respiration, by which the RR interval on an ECG or PPG is shortened during inspiration and prolonged during expiration. The effect of RSA on the PPG waveform is such that inhalation gradually increases the HR while decreasing the PPG waveform amplitude, whereas exhalation gradually decreases the HR while increasing the PPG waveform amplitude. In particular embodiments, the effect of RSA on the PPG waveform may be factored into and separate from the determination of noise in the PPG waveform (e.g., N=3 is chosen to fall within the known RSA cycle).

On the other hand, if it is determined that there is noise present in the delay-filtered signal 234 (e.g., step 246), then as illustrated in the example of FIGS. 2A-2C, noisy data 256 is sent to delay 258 of a waveform builder 250. In particular embodiments, waveform builder 250 may include a statistics engine 252, delay 258, and blender 262. In particular embodiments, the delay-filtered signal 234 processed through waveform buffer 244 is inputted into statistics engine 252, which then generates a statistical waveform 254 based on the data stored in waveform buffer 244 (e.g., the last 3 pulses), and the data may also be adjusted to match the changing period of the signal to allow for better signal matching as the PPG waveform signal goes from noisy to clean and the statistical waveform 254 is transitioning to real-time data. This statistical waveform 254 is then sent to blender 262. In addition, noisy data 256 is inputted into delay 258, where it is stored for a predetermined amount of time such that the statistical waveform 254 may be generated by statistics engine 252 (e.g., allowing for signal correction in approximately real-time). Then, delay-noisy data 260 and the statistical waveform 254, in addition to the determination from noise detector 240 and the delay-filtered signal 234 (e.g., output by data gate 238), are inputted into blender 262. Blender 262 may then blend the statistical waveform 254 (e.g., the constructed waveform) with the delay-filtered signal 234 (e.g., the raw-signal waveform) when noise is detected in the delay-filtered signal 234. As an example and not by way of limitation, the blending may include beginning with zero strength (e.g., 0%) given to the constructed waveform and 100% strength given to the raw-signal waveform at the point nearest to the a selected feature (e.g., the zero-crossing, the peak, or the trough), and then progressively weighing the constructed waveform more heavily until the signal is 100% constructed waveform and 0% raw-signal waveform. In addition, this process may be gradually done in reverse to merge two signals after noise is no longer detected in the signal. In particular embodiments, the resultant blended signal may then be sent through an additional filter to ensure points on the waveform are smoothly blended into this resultant, blended signal. Then, blender 262 may output noise-compensated data 264 (e.g., a noise-compensated signal), to a pulse corrector 270.

As illustrated in the example of FIGS. 2A-2C, pulse corrector 270 may include a heart rate (HR) calculator 272, a RSA interpolator, a RSA quality check 280, and an OR gate 286. The purpose of pulse corrector 270 is to take into account the RSA cycle when suggesting the HR in the presence of the noisy signal, which may be done using quadratic interpolation of the HR signal. First, noise-compensated data 264 is inputted into HR calculator 272 to determine a heart-rate signal based on the noise-compensated data 264. Then, the heart-rate signal determined via HR calculator 272 is sent to RSA interpolator, which calculates a quadratic-fit signal 276 (e.g., an interpolated RSA-estimate), and compares that with a noise-compensated HR signal 278 via RSA quality check 280. If it is determined that the quadratic-fit signal 276 deviates from the noise-compensated HR signal beyond a predetermined amount (e.g., a threshold amount of acceptable deviation), that is, if it is determined that the noise-compensated HR signal 278 is of poor quality, then a quadratic average signal 282 is calculated based on both the quadratic-fit signal 276 and the noise-compensated HR signal 278, and this quadratic average signal 282 is outputted via OR gate 286 as the corrected output 290 (e.g., an outputted signal that is corrected in approximately real-time). On the other hand, if it is determined that the quadratic-fit signal 276 does not deviate from the noise-compensated HR signal beyond the predetermined amount, then the noise-compensated HR signal 284 is outputted via OR gate 286 as the corrected output 290. In particular embodiments, the threshold amount of acceptable deviation may depend on the circumstances. As an example and not by way of limitation, when no noise is detected, the maximum allowable deviation between a first set of data and a second, subsequent set of data may be 15%. However, when noise is detected, the maximum allowable deviation between the first set of data and the second, subsequent set of data may be decreased to 5%.

In particular embodiments, features (e.g., peaks, zero crossings, or troughs) of the PPG waveform are used to measure beat-to-beat times that then are used to determine HRV. Example embodiments dynamically select features to use to determine the beat-to-beat times based on determining whether a particular feature of the waveform is corrupted by noise. In particular embodiments, uncorrupted features found in consecutive heart beats are used to determine the beat-to-beat time. As an example and not by way of limitation, noise correction system 200 attempts to determine peaks of the sensor signal having certain properties such as a well-formed morphology with repeating and detectable features in each cycle (e.g., a sinusoidal-type signal in the proximity of the peak in a PPG signal). In particular embodiments, peak detection is performed and signal features are determined based on the detected peak information.

In accordance with example embodiments, noise can be computed in a variety of different ways. One approach of an example embodiment is to compute the noise as the ratio of the total area of the signal with the average signal in the clean PPG signal. If this ratio is significantly outside the expected range then the signal can be deemed noisy, and this ratio can serve to quantify the level of the noise. Another approach of an example embodiment is to estimate the number of peaks (or troughs) in the given pulse and if the given number is above a threshold then this is a quantifier of the noise in the signal. Yet another approach of an example embodiment is to measure the root-mean square (RMS) deviation of the signal from the expected profile and this measure can be taken as the noise level of the signal. Yet another of an example embodiment is that for each peak and trough and zero crossing that is calculated, the expected signal profile in the vicinity of such features is calculated by curve fitting. Then the RMS deviation of the actual signal from the expected signal is used as the quantification of the overall noise in the signal for the given feature. As a further refinement of this approach, if a particular feature of the signal is used for the RR calculation then the noise in the vicinity of that feature is used as the marker of the noise in the signal.

One particular error-noise model may be more suited for error correction in a given setting, and that particular noise model may be taken as the preferred model. In an example embodiment, noise correction system 200 automatically determines which error-noise model is to be selected. For instance, synthetic noise may be introduced in a clean PPG and the accuracy of correction of each error-noise model measured. The error-noise model with the highest accuracy (e.g., lowest error) is selected.

Further, in a number of situations, the signal may be so corrupted that it is not possible to estimate any feature at all. In such a case, the number of such pulses (obtained by the extrapolation from the average heart rate) in the overall signal is used as a marker of overall noise in the signal. However, each noisy RR may corrupt, e.g., three RR-delta measurements. Hence, the noise that is discretely distributed in the signal may have a larger effect than noise that is present in a continuous stretch. For example, if the noise only affects one pulse, and such single noisy pulse instances are distributed throughout the signal then it can lead to, e.g., 30 noisy RR-delta computations and hence this case corrupts the signal more than the case where, e.g., 10 noisy pulses are consecutive. This information about the total expected number of RR-delta that are either erroneous or are simply not calculable can be a meaningful quantification of the total noise in the signal.

In particular embodiments, quantifying an amount of noise of the PPG signal includes quantifying an amount of noise associated with predetermined features of the PPG waveform. As discussed below, predetermined features of the PPG waveform may include one or more peaks associated with the PPG signal, one or more troughs associated with the PPG signal, one or more zero-crossings associated with the PPG signal, or any combination thereof. In particular embodiments, PPG waveforms may be acquired from the user's wrist at different sampling rates using an sensor platform that includes LEDs and photodetectors (e.g., as part of wearable device 110B). Data received from wearable device 110B may be digitized at varying frequencies, for example, in a range from 25 Hz to 800 Hz. As an example and not by way of limitation, a time series of the PPG waveforms may contain a number of peaks (e.g., 4 peaks) and the morphological features of the PPG waveform may change between each of the peaks.

In particular embodiments, features of the PPG waveform are selectively used based on the determined noise level of each feature. In addition, the signal in the vicinity of each feature is analyzed to determine whether noise is present and determine whether the feature is a reliable feature. As an example and not by way of limitation, if a peak of the PPG signal is determined to be noisy, the RR interval may be calculated not from a first peak to a second, subsequent peak, but from a zero-crossing to a subsequent zero-crossing. In other words, noise correction system 200 may analyze all features associated with a signal to select one or more features to use in signal analysis based on the noise in one or more of the features, and also discard any feature that are determined to be noisy.

In particular embodiments, the noise error estimation is computed, as described above, and the noise in the signal is quantified to generate a noise-error curve, which may then be used to correct the computed HRV, as discussed below. In particular embodiments, cardiac activity data may include a PPG signal measured over a noise-calculation period. As described above, a noise level of the received sensor data based on calculating an error-noise estimation associated with the PPG signal, and then quantifying an amount of noise of the PPG signal based on the error-noise estimation associated with the PPG signal.

In particular embodiments, noise correction system 200 may adjust the health-variability measurement by an amount calculated based on the determined noise level. In particular embodiments, adjusting of the health-variability measurement by the amount calculated based on the determined noise level may include decreasing the health-variability measurement an amount determined by the calculated error-adjustment. As the percentage of noise increases in the signal, the percentage of resultant error also increases. Thus, a noisy signal may result in an artificially elevated (and thus inaccurate) HRV computation and thus an artificially decreased SVB computation in comparison with the signal after noise compensation. With noise compensation, the SVB is adjusted upward by the error determined based on the noise level and the error-noise curve in order to obtain a more accurate SVB of the user. In particular embodiments, after adjusting the HRV measurement, noise correction system 200 may send the adjusted HRV measurement to the electronic device of the user (e.g., client system 120). Although this disclosure describes or illustrates particular types of components and uses of these components of noise correction system 200, this disclosure contemplates any suitable types of components for noise correction of cardiac or brain-wave activity data.

The cardiovascular system is regulated by the ANS, that includes the sympathetic nervous system (SNS) and parasympathetic nervous systems (PSNS). Sympathovagal balance (SVB) is defined as the equilibrium point between the SNS and the PSNS. The rhythm of the heart is controlled by the sinoatrial (SA) node, which is modulated by both the sympathetic and parasympathetic branches of the autonomic nervous system. The heart receives its neural input through parasympathetic and sympathetic ganglia and lateral grey column of the spinal column. Sympathetic activity tends to increase heart rate, while parasympathetic activity tends to decrease heart rate. In particular embodiments, evaluation of emotions based at least in part on SVB looks at the homeostatic equilibrium where the sympathetic outflow and PSNS (e.g., vagal nerve) outflow are in stable balance. Accordingly, SVB may be determined by analyzing relative dominance and balance between the SNS and PSNS (e.g., between parasympathetic outflow and sympathetic outflow). This approach is linear in nature, which makes it very stable to noise (e.g., which tends to be non-linear in nature). In addition, this approach is highly customizable to address the unique needs of the user, other users, or medical professionals.

Figure 3A:
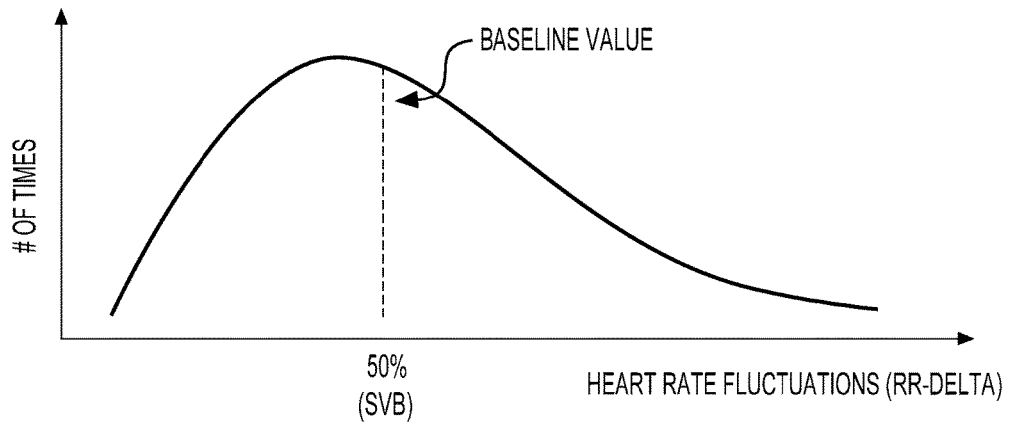
FIG. 3A illustrates an example of a baseline data histogram.

FIG. 3A illustrates an example of baseline data histogram 300. As illustrated in example of FIG. 3A, a x-axis of baseline data histogram 300 corresponds to heart rate fluctuations (e.g., RR-deltas or RR interval differences between successive heart beats), and a y-axis of baseline data histogram 300 corresponds to a frequency or number of times particular heart rate fluctuations occur for a set of baseline data. A portion of a set of measurement data that is on one side of the baseline SVB is used to determine a number of ANS activity markers within a first portion of cardiac activity data. A HRV characteristic that is a ratio involving the number of ANS activity markers within the first portion and the number of ANS activity markers within a second portion of the cardiac activity data is calculated. The SVB is defined by the point of 50:50 distribution of baseline data histogram 300 such that 50% of the data points of the set of baseline data are to the left of the SVB and 50% of the data points of the set of baseline data are to the right of the SVB. HRV data is used to determine changes in the SVB. HRV describes the variations between consecutive heartbeats. Using baseline data histogram 300, the SVB corresponds to a HRV zone representative of a "normal" (e.g., non-stressed) state. The analysis of SVB described treats the SNS and PSNS with equal weightage (e.g., because they are both useful in analyzing the ANS arousal) and uses the RR-deltas.

In particular embodiments, to determine SVB, stress or arousal is defined as increased dominance of the SNS in the RR-delta histogram $H_t$ of test data t, and the data points on the histogram correspond to the difference between lengths of adjacent RR intervals in a set of test data. In particular embodiments, a ratio of a number of events relatively mapped to SNS with a number of events relatively mapped to PSNS is computed. Measurements of HRV may be based on time-domain analysis or frequency domain analysis, which both have numerous shortcomings. As an example, frequency domain analysis methods such as those based on FFT, are not very suitable for implementation on mobile platforms since they are extremely sensitive to the noise artifacts, and require rather long measurement time periods. Time domain methods, such as root mean square of successive heartbeat interval differences (RMSSD), standard deviation of NN (beat-to-beat) intervals (SDNN), and the proportion of the number of pairs of successive NNs that different by more than 50 millisecond divided by the total number of NNs (pNN50), are frequently used to analyze the instantaneous heart-rate signal. Given a baseline SVB of the user, and an RR-delta histogram $H_t$, the SVB may be computed as a median of all RR-deltas, a mean value of all RR-deltas, 50% of RMSSD, computed over $H_t$, 50% of SDNn, computed over $H_t$, other relevant values, or any combination thereof.

Figure 3B:
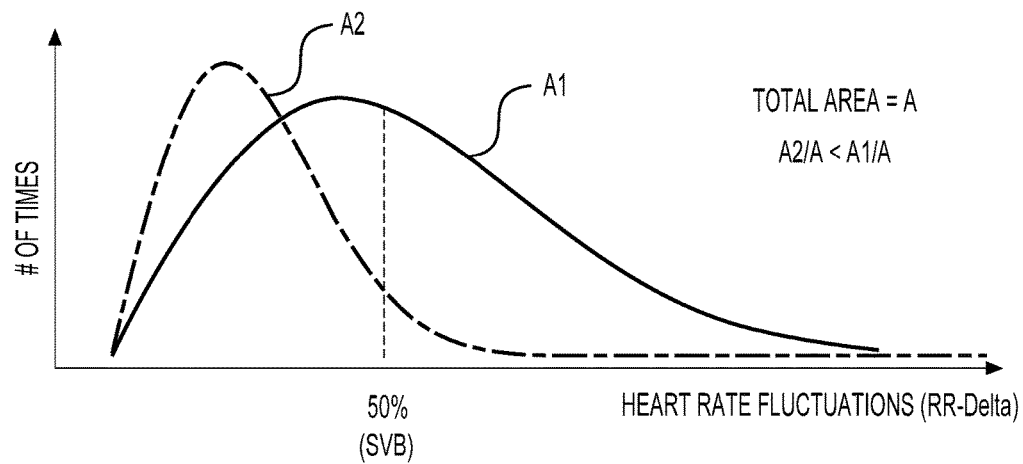
FIG. 3B illustrates an example of a test data histogram in which a sympathovagal balance is shifted to the left.
Figure 3C:
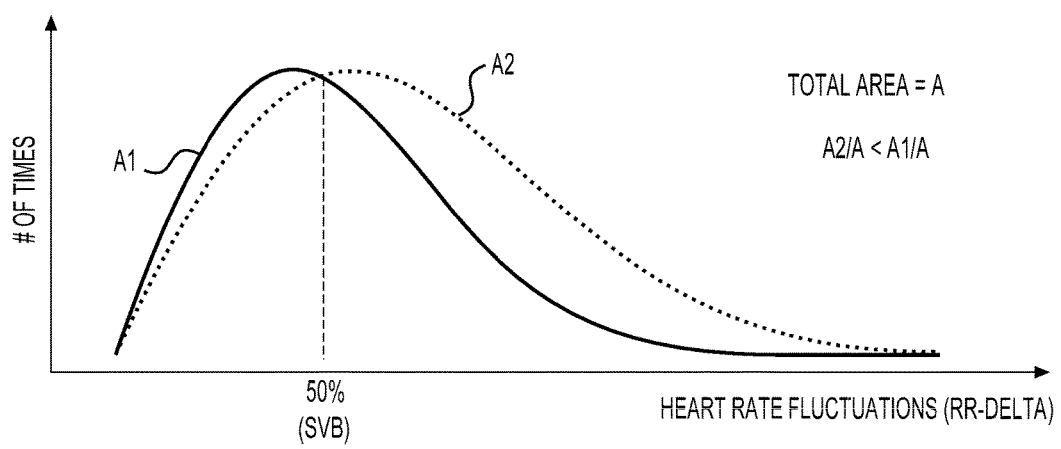
FIG. 3C illustrates an example of a test data histogram in which a sympathovagal balance is shifted to the right.

FIG. 3B illustrates an example of a test-data histogram 310 in which the SVB is shifted to the left, and FIG. 3C illustrates an example of a test-data histogram 320 in which the SVB is shifted to the right. As illustrated in the example of FIG. 3B, similar to FIG. 3A, an x-axis of test data histogram 310 corresponds to heart rate fluctuations (e.g., RR-deltas), and a y-axis of test data histogram 310 corresponds to a number of times of the heart rate fluctuations for a set of test data. In particular embodiments, the first and second portions of the set of measurement data are selected based on a baseline SVB value (e.g., a user-specific baseline SVB value) that divides a histogram representation of the set of measurement data into the first and second portions. When the heart rate fluctuations for the set of test data on average results in the shifting of balance from histogram A1 (e.g., corresponding to the baseline data) toward a left direction to histogram A2, or in other words, the number of measurements of heart rate fluctuations of histogram A2 that are to the left of the SVB (e.g., as determined based on the baseline data) are greater than the number of measurements of heart rate fluctuations of histogram A2 that are to the right of the SVB, then it is determined that the user's state corresponds to a HRV zone representative of a "high arousal" state. Explained another way, as shown in FIG. 3B, given a total area A, the area of A2 over A (e.g., the area under the curve of A2) is determined to be less than the area of A1 over A (e.g., the area under the curve of A1) when the histogram shifts to the left and it is determined that the user's state corresponds to a HRV zone representative of a "high arousal" state or increased SVB.

On the other hand, as shown in FIG. 3C, similar to FIG. 3A, an x-axis of test-data histogram 320 corresponds to heart rate fluctuations (e.g., RR-deltas), and a y-axis of test-data histogram 320 corresponds to a number of times of the heart rate fluctuations for a set of test data. When the heart rate fluctuations for the set of test data on average results in the shifting of balance from histogram A1 (e.g., corresponding to the baseline data) toward a right direction to histogram A2, or in other words, the number of measurements of heart rate fluctuations of histogram A2 that are to the right of the SVB (e.g., as determined based on the baseline data) are greater than the number of measurements of heart rate fluctuations of histogram A2 that are to the left of the SVB, then it is determined that the user's state corresponds to a HRV zone representative of a "low arousal" state. Explained another way, as illustrated in example of FIG. 3C, given a total area A, the area of A2 over A (e.g., the area under the curve of A2) is determined to be greater than the area of A1 over A (e.g., the area under the curve of A1) when the histogram shifts to the right and it is determined that the user's state corresponds to a HRV zone representative of a "low arousal" state.

Particular embodiments of this embodiment depend on creatively dividing the RR-delta histogram, $H_T$, based on the notion of contextually appropriate SVB. As an example and not by way of limitation, if the context is all the cyclic components responsible for variability in the period of recording, then the ratio for SVB may be evaluated via the SDNN(H) model.

In particular embodiments, a length of a buffer of the RR-delta data that is used to populate the histogram need not be limited to some fixed size during the computation of stress. Since the algorithm provides a measure of SVB, even if a longer length of data is used, above a certain minimum length, the SVB would nonetheless be meaningfully depicted. As such, the buffer length may be varied based on the requirements of accuracy, stability, or any other attribute where a variable length may be beneficial. In particular embodiments, measurement data may include variations in the beat to beat heart rate (RR-delta), skin conductance, frequency components inherent in electrical activity on scalp, inhalation and exhalation patterns, etc. As an example and not by way of limitation, the measurement data can be measured using heart rate measurement sensors such as electrocardiogram (ECG), electrodermal analysis sensors, EEG headset, respiration sensors, other suitable sensors, or any combination thereof.

Figure 4:
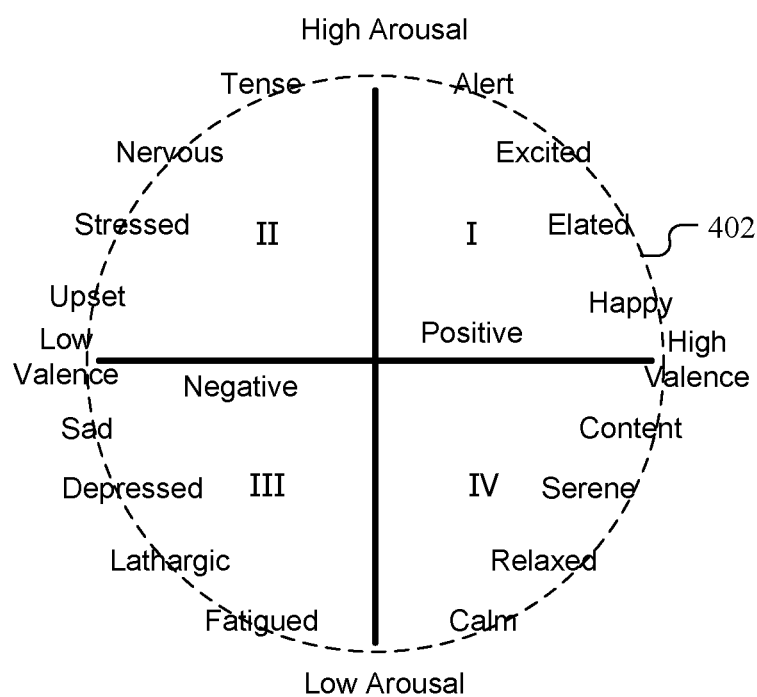
FIG. 4 illustrates an example diagram of the circumplex model of emotion.

FIG. 4 illustrates an example diagram of the circumplex model of emotion. The circumplex model of emotions 400 maps human emotions into a two-dimensional circular space 402 containing arousal and valence dimensions. Levels of arousal are mapped to the vertical axis and the valence is mapped to the horizontal axis of circular space 402. In the circumplex model 400, the valance corresponds to a type of emotion (e.g., positive or negative) while the arousal corresponds to an intensity of the emotion. The center of circular space 402 represents neutral valence and arousal levels. In this model, emotional states can be represented at any level of valence and arousal, or at a neutral level of one or both of these factors. In addition, circular space 402 may be partitioned in four quadrants I-IV that each correspond to a grouping of emotional states with similar levels of arousal and valance. As an example and not by way of limitation, quadrant I emotions correspond to positive valance and high-arousal emotional states. In the illustrated embodiment, emotional states of quadrant I comprise alert, excited, elated, and happy. In order of increasing valence, these emotional states of quadrant I are alert, excited, elated, and happy. In order of increasing arousal, these emotional states of quadrant I are happy, elated, excited, and alert.

Quadrant II emotions correspond to negative valence and high-arousal emotional states. In the illustrated embodiment, emotional states of quadrant II comprise tense, nervous, stressed, and upset. In order of increasing valence, these emotional states of quadrant II are upset, stressed, nervous, and tense. In order of increasing arousal, these emotional states of quadrant II are upset, stressed, nervous, and tense.

Quadrant III emotions correspond to a negative valance and low-arousal emotional states. In the illustrated embodiment, emotional states of quadrant III comprise sad, depressed, lethargic, and fatigued. In order of increasing valence, these emotional states of quadrant III can be listed as sad, depressed, lethargic, and fatigued. In order of increasing arousal, these emotional states of quadrant III are fatigued, lethargic, depressed, and sad.

Quadrant IV emotions correspond to positive and low-arousal emotional states. In the illustrated embodiment, emotional states of quadrant IV comprise calm, relaxed, serene, and content. In order of increasing valence, these emotional states of quadrant IV are calm, relaxed, serene, and content. In order of increasing arousal, these emotional states of quadrant IV are calm, relaxed, serene, and content. It will be appreciated that additional emotions can be included, or one or more emotions of FIG. 4 can be omitted or renamed, in alternative example embodiments.

As described below, an estimate of the emotional of a user is computed or determined based at least in part on cardiac-activity data (e.g., heart rate or SVB) and in conjunction with "brain-wave" activity data (e.g., EEG data) measured via the sensors or the devices 110A, 110B of FIG. 1.

Figure 5:
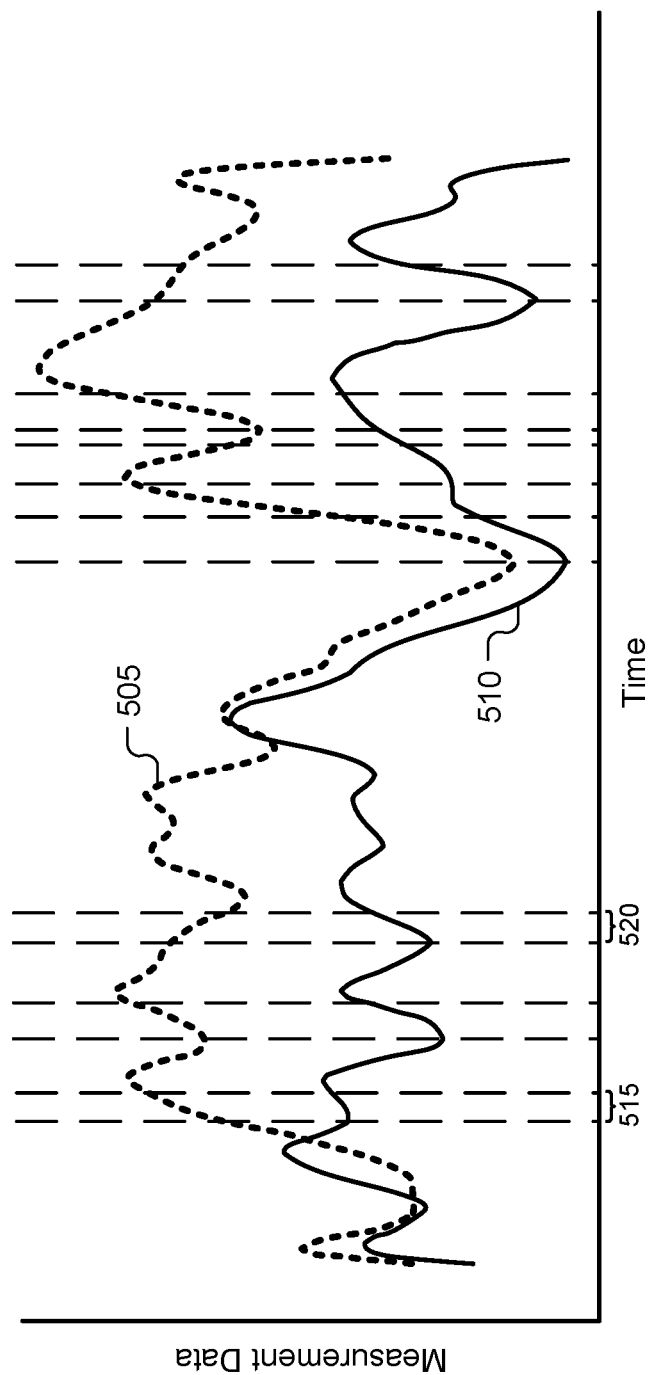
FIG. 5 illustrates example cardiac and brain-wave activity data as a function of time.

FIG. 5 illustrates example cardiac and brain-wave activity data as a function of time. The data from wearable devices 110A-B can compute SVB data 510 (e.g., based on HR and SVB) and EEG short-term excitement (STE) data. Positive-valance emotions (e.g., happiness or excitement) are emotions that may have short duration. Example methods and systems disclosed herein for computing SVB can facilitate estimating emotional states having short duration, as illustrated in FIG. 5. For instance, in particular embodiments, emotion evaluation is based on an amount of covariance or how much SVB and EEG (as well as HR in example cases) change in unison.

As an example and not by way of limitation, periods of time can be marked as memorable and/or non-memorable based on whether HRV and EEG-STE values varied during a period of time. For instance, SVB data 510 and EEG-STE data 505 are both increasing during time period 515. As another example, SVB data 510 is increasing, while EEG-STE data 505 is decreasing during time period 520. As such, both time periods 515, 520 can be marked as memorable. Furthermore, a high/rising SVB level is treated as an indicator of a positive emotional state. Additionally, a rising (or falling) EEG-STE level in combination with high/rising SVB level can be used to mark the corresponding time duration as Excitement (or as Thrill).

Figure 6:
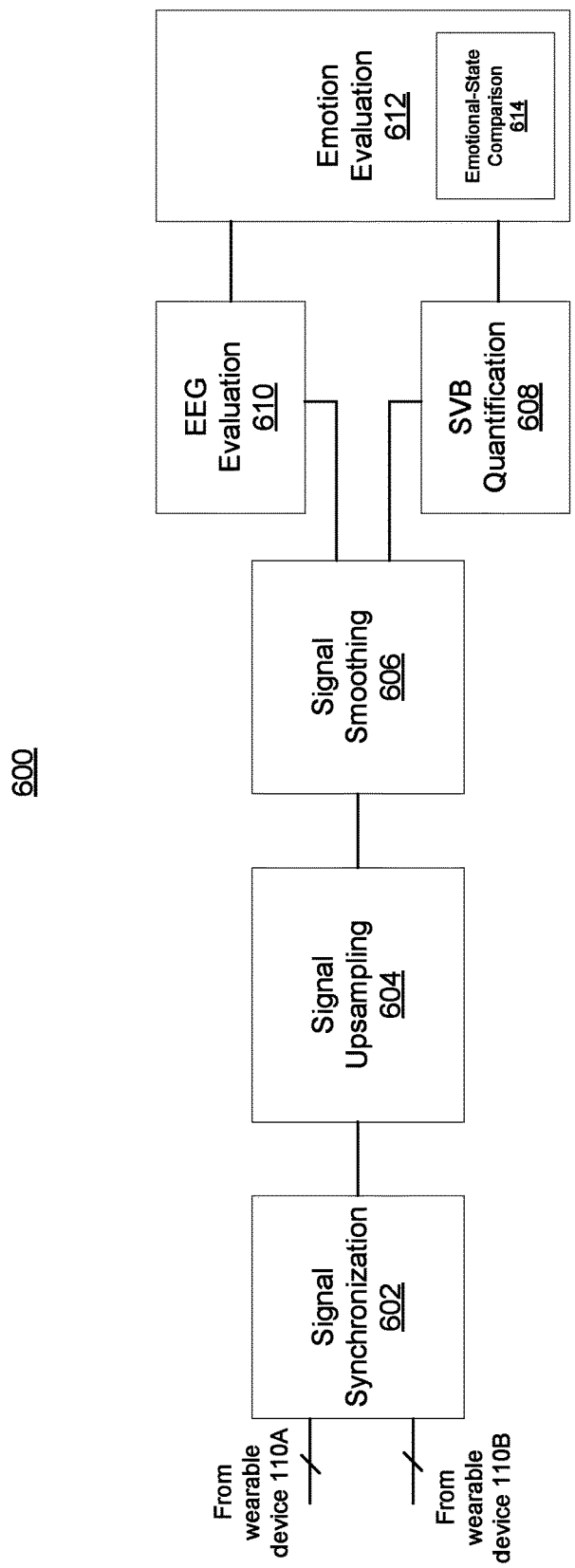
FIG. 6 illustrates an emotion evaluation system for emotion evaluation.

FIG. 6 illustrates an emotion-evaluation system 600 that facilitates applications utilizing emotion evaluation. In particular embodiments, emotion-evaluation system 600 may include a signal-synchronization module 602, signal-upsampling module 604, signal-smoothing module 606, SVB-quantification module 608, EEG-evaluation module 610, and emotion-evaluation module 612. Herein, reference to a module may refer to self-contained computer code or executable that is configured to perform a discrete function. Furthermore, a module may be a dedicated electronic circuit configured to perform the discrete function. In particular embodiments, signal-synchronization module 602 initially synchronizes signals captured by wearable devices 110A-B, described above. As an example and not by way of limitation, signal-synchronization module 602 transmits signals to synchronize the sensors of wearable device 110A configured to capture brain-wave activity (e.g., EEG) with the sensors of wearable device 110B configured to capture the heart activity (e.g., ECG or PPG), such that both data streams represent information captured at approximately the same period of time. For example, an amount of time difference between the time stamps of each type of data (e.g., EEG or PPG) may be less than 0.1 milliseconds. In the case of cardiac activity data, a large difference in the time stamps of the data may cause difficulty in determining the HRV.

Signal-upsampling module 604 receives the data from wearable devices that has been synchronized by signal-synchronization module 602. In particular embodiments, both data streams are interpolated to produce an approximation of the signal as if it were obtained by sampling the signal at a higher rate (e.g., to 1 KHz or higher). The covariance of the data streams may be analyzed on a data stream (e.g., brain-wave or cardiac activity) whose rate of perturbation is approximately the same as the rate of a typical heartbeat. As an example and not by way of limitation, the upsampling may be performed by upsampling the vicinity of one or more features being used to calculating the HR, HRV, or EEG information, as described above.

As illustrated in the example of FIG. 6, signal-smoothing module 606 receives the upsampled data streams from signal-upsampling module 604 and removes noise from the upsampled data streams. In particular embodiments, signal-smoothing module 606 removes noise introduced by RSA, as described above with regard to the example of FIGS. 2A-2C, from cardiac-activity data. As an example and not by way of limitation, RSA noise may be filtered using a smoothing filter (e.g., low-pass filter) for 4 heart beats corresponding to a typical breathing rate of approximately 4 heart beats. As an example and not by way of limitation, the covariance in heart rate may be compared against changes in HRV or EEG once the noise is removed from the cardiac-activity data, since the presence of RSA noise makes determining covariance between cardiac-activity data and EEG signals difficult.

The processed cardiac-activity and brain-wave data of the signal-smoothing module 606 is transmitted to the SVB-quantification module 608 and EEG-evaluation module 610, respectively. In particular embodiments, SVB-quantification module 608 computes the HRV-based SVB by analyzing a histogram of HRV measured at pre-determined time intervals (e.g., every 30 seconds), as illustrated in the example of FIGS. 3A-C. As described above, SVB is defined as the equilibrium point between the SNS and the PSNS, therefore the time requirement for accurate SVB calculations is dependent on the stabilization times for the SNS and PSNS measurement. As an example and not by way of limitation, PSNS measurements may take approximately 2 to 3 seconds to stabilize whereas SNS measurements may take approximately 25 seconds. Histograms with larger bins (or longer measurement times) compensate for latency of the system, while smaller bins (or smaller measurement times) may lead to inaccurate SVB calculations.

In an example embodiment, SVB and HR are not binary but rather quantify the intensity of SVB and HR activation. Accordingly, the computed intensities can be used to increase the resolution and number of emotional states that can be estimated.

It can take a certain length of time before the brain can process an emotion by higher-order centers of the brain. For example, this time period can be 6 seconds or more. Given the fact that a typical breathing cycle of users is around 4 second per breath which leads to respiratory sinus arrhythmia (RSA) based variations in HR and HRV and SVB, example embodiments use a time window (e.g., 10 seconds) to affirm the covariant trend from the signals from central nervous system (picked by EEG) and cardiac signals (picked by an appropriate cardiac-activity measurement sensor).

As described above, brain-wave data may be a stream of EEG measurements from multiple sensors that are each placed to measure activity from a particular region of the brain. For example, the EEG sensors can be arranged to generate 14 EEG channels: AF3, F7, F3, FC5, T7, P7, O1, O2, P8, T8, FC6, F4, F8, and AF4 (based on the International 10-20 locations). In particular embodiments, EEG-evaluation module 610 may execute a features evaluation process to determine features of the brain-wave data. The features extracted brain-wave measurements may be mapped into an n-dimensional feature vector. A feature vector is a vector of numerical "features" or independent variables that represent an output, in this case the emotion of the user indicated by EEG data. In particular embodiments, the feature vector collected and sent by wearable device 110A may include several extracted features from the EEG data. In particular embodiments, the features data or feature vectors may be stored on any suitable database such as data store 140.

Classification is the correlation of an output to a given input (e.g., emotion to brain-wave and cardiac data). For example, a particular feature vector (e.g., an ordered list of features) may be correlated to a particular emotion of the user. Classification may be performed using a predictor function that is constructed using a set of "training" data that includes an input vector and an answer vector. A machine-learning classifier algorithm may combine (e.g., through a dot product) the input vector with one or more weights to construct a predictor function to best fit the input vector to the answer vector. As an example and not by way of limitation, classification algorithms may include support vector machine (SVM), Naive Bayes, Adaptive Boosting (AdaBoost), Random Forest, Gradient Boosting, K-means clustering, Density-based Spatial Clustering of Applications with Noise (DBSCAN), or Neural Network algorithms.

In particular embodiments, during offline training, the training data may be obtained from the cardiac and brain-wave data from a number of users and the corresponding emotion of the user at the time the data is being measured. As an example and not by way of limitation, the input vector may be a vector of the extracted EEG features and the answer vector may be the corresponding emotion (e.g., happiness) as reported by the user. As an example and not by way of limitation, training data for emotional state characteristic evaluation may be captured from the users watching a content (e.g., a sports game, TV show, or movie) while wearing wearable devices 110A-B. In particular embodiments, the output vector of the machine-learning classifier may be one or more quadrants or emotion of circumplex model 400 or an emotional state characteristic, as described below, and the output vector may be compared to the answer vector to "train" the predictor function of the machine-learning classifier.

In an example embodiment, the EEG evaluation module 610 outputs one or more state characteristic that may include EEG-excitement, EEG-engagement, EEG-frustration, and EEG-amygdala levels. The EEG-amygdala level can be combined with HR data to determine the levels of EEG-Q2 and EEG-Q3. For example, increasing HR indicates EEG-Q2 activation and decreasing HR indicates EEG-Q3 activation. The respective outputs can be a numerical value indicating the strength of the classification based on the received EEG data. As stated above, the outputs of the EEG evaluation module 610 can be combined with the SVB quantification to provide an estimate of emotional state of the user.

As illustrated in the example of FIG. 6, emotion-evaluation module 612 receives cardiac-activity (e.g., HR and SVB) data, and brain-wave (e.g., EEG) data from SVB quantification module 608 and EEG-evaluation module 610, respectively. In particular embodiments, emotion-evaluation module 612 is configured to determine emotions of the user based on the covariance of HR, SVB, and EEG data over a significant period of time (e.g., ~5 or more seconds). In particular embodiments, emotion evaluation module 612 performs an estimation of emotional state of the user during a period of time based on the data from SVB-quantification module 608. In particular embodiments, emotion-evaluation module 612 may include an emotional-state comparison module 614. In particular embodiments, moments in time corresponding to predetermined thresholds of cardiac-activity and brain-wave data may be used initiate the evaluation of emotions of the user. As an example and not by way of limitation, moments in time corresponding to thresholds (e.g., HRV rising above 60 and excitement in EEG rises above 80) may be captured and associated with a particular emotion (e.g., elation or excitement).

In particular embodiments, emotion-evaluation module 612 identifies emotions based on determining a particular quadrant of the circumplex model of emotion 400 that corresponds to the SVB and HR data transmitted by SVB-quantification module 608. As an example and not by way of limitation, emotion-evaluation module 612 may compute that SVB and HR both increasing at substantially the same time corresponds to quadrant I (upper-right quadrant) of the circumplex model 400, SVB decreasing and HR increasing corresponds to quadrant II (upper left quadrant), SVB and HR both decreasing corresponds to quadrant III (lower-left quadrant), and SVB increasing and HR decreasing corresponds to quadrant IV (lower-right quadrant). In particular embodiments, the determined emotions of the user may be refined using other bio-sensing measurement. As an example and not by way of limitation, decreased SVB and increased HR with concomitant increase peripheral body temperature may correspond to anger. As another example, decreased SVB and increased HR with concomitant increase in fidgetiness or movement measured by an accelerometer may correspond to nervousness. In particular embodiments, emotion-evaluation module 612 refines the emotion of the user within the particular quadrant of the circumplex model 400 based on the emotion of the user determined by EEG-evaluation module 610. As an example and not by way of limitation, emotion-evaluation module 612 refines on the covariance of a combination HR, SVB, or EEG data to particular emotions. For example: EEG-excitement increasing and SVB increasing may be evaluated as Excitement; EEG-excitement and SVB increasing may be evaluated as Thrill; EEG-excitement neutral and SVB increasing may be evaluated as Peace; EEG-excitement, HR, and SVB increasing may be evaluated as Joy; HR and SVB increasing may be evaluated as Elated/Happy; EEG-Engagement and SVB increasing may be evaluated as Engagement; EEG-excitement and HR decreasing and SVB may be evaluated as Contentment; EEG-Engagement and HR increasing may be evaluated as Alert; EEG-Frustration increasing and HRV decreasing may be evaluated as Frustration; EEG-Q3 increasing, and SVB and HR decreasing may be evaluated as sadness; and EEG-Q2 increasing, SVB decreasing, and HR increasing may be evaluated as Anger.

SVB and HR decreasing is indicative of emotions in quadrant III (e.g., sadness, depression, boredom, or lethargy) of circumplex model 400. Furthermore, the analysis of sadness may be refined through detection of a concomitant (e.g., high covariance) decrease or increase in EEG activity measured by EEG-evaluation module 610. Continued decrease in EEG activity along with decreased SVB and HR for a long period of time (e.g., extending over several days) may be indicative of depression. As another example, SVB decreasing and HR increasing is indicative of emotions in quadrant II (e.g., upset, stress, nervous, or tension) of circumplex model 400. In particular embodiments, the analysis of anger is refined through detection of a concomitant decrease or increase in EEG activity measured by EEG-evaluation module 610. In particular embodiments, emotion-evaluation module 612 refines the emotion of the user within the particular quadrant of the circumplex model 400 based on the emotion of the user determined by EEG-evaluation module 610.

As used herein, increases and decreases in EEG, SVB, and HR levels are relative to baseline values.

In an example embodiment, if the trend in the coherence of EEG signal and heart signal (in terms of SVB or HR or both) holds for more than a predetermined amount of time (e.g., 10 seconds), then the system outputs the estimated emotional state. It will be appreciated that other embodiments omit checking for coherence of the EEG signal and heart signal for a predetermined amount of time.

In particular embodiments, emotional-state comparison module 614 determines the emotion of the user comparing emotions concomitantly determined by SVB-quantification module 608 and EEG-evaluation module 610. As described above, SVB-quantification module 608 estimates the emotions of the user based on SVB and HR, while EEG-evaluation module 610 estimates the emotions of the user based on classifying EEG features. In particular embodiments, emotional-state comparison module 614 estimates the emotion of the user based on determining there is a correspondence between the emotion estimated by SVB-quantification module 608 with the emotion estimated by EEG-evaluation module 610. As an example and not by way of limitation, emotional-state comparison module 614 may estimate the user is feeling elated based on SVB-quantification module 608 determining both SVB and HR increasing, and at the same time EEG-evaluation module 610 determines the user is experiencing a positive emotion that is classified as elation.

Figure 7:
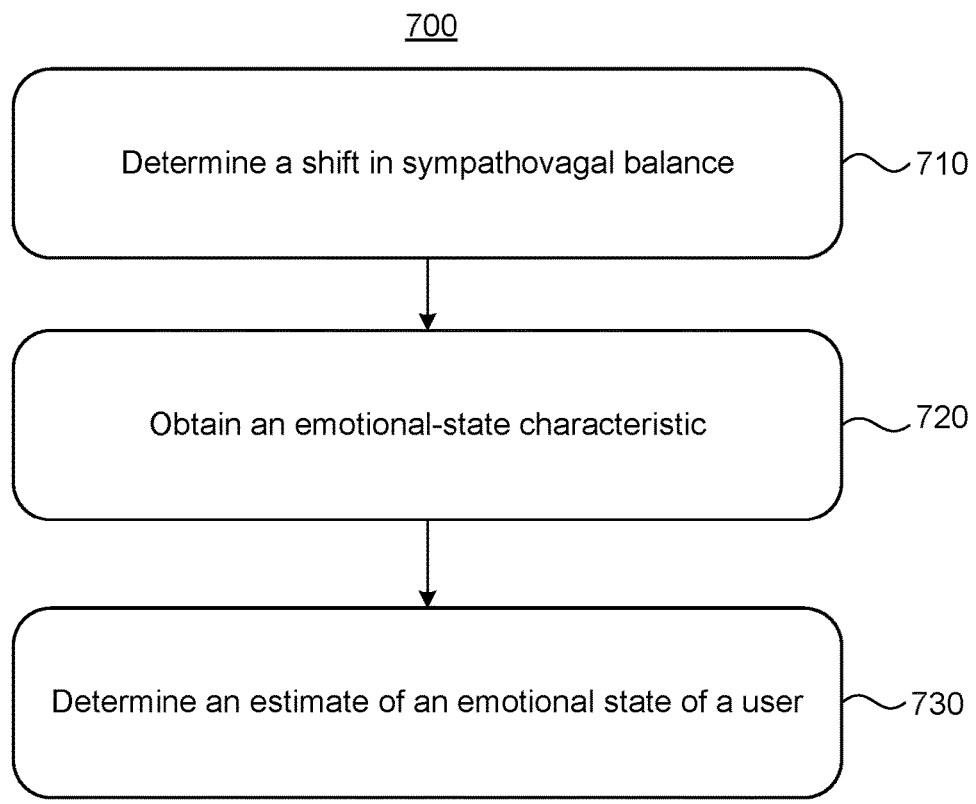
FIG. 7 illustrates an example method for emotion evaluation.

FIG. 7 illustrates an example method for emotion evaluation. As described below, the emotions of the user may be evaluated by correlating the features of brain-wave activity and cardiac activity to particular emotions. The example method 700 may be deployed on one or more electronic devices, such as a mobile phone, tablet computer, smart watch, head-mounted device, body-harness-secured devices, and the like mobile devices, wearable devices, fixed-location computing devices, and/or network or cloud deployed systems, having suitable communication, processing, sensing facilities, other suitable devices, or any combination thereof. In particular embodiments, measurement data may include variations in the beat to beat heart rate (RR-delta), skin conductance, frequency components inherent in electrical activity on scalp, inhalation and exhalation patterns, etc. As an example and not by way of limitation, the measurement data can be measured using heart rate measurement sensors such as electrocardiogram (ECG), electrodermal analysis sensors, EEG headset, respiration sensors, other suitable sensors, or any combination thereof. As another example and not by way of limitation, a processor or circuitry may embody the method (e.g., one or more computer processors may be communicatively coupled to a data storage device that stores instructions executable by the one or more computer processors to perform operations of example method 700 for emotion evaluation).

In particular embodiments, the method 700 may be performed by emotion-evaluation system 600. The method 700 begins at step 710, where emotion-evaluation system 600 determines a shift in SVB over a period of time. In particular embodiments, the shift in SVB may be determined by SVB-quantification module 608 using cardiac-activity data captured by sensors of wearable device 110B. At step 720, emotion-evaluation system 600 may obtain an emotional state characteristic of the user based on brain-wave activity data. In particular embodiments, emotion-evaluation module 612 may estimate the emotional state characteristic may be determined by EEG-evaluation module 610 using brain-wave data captured by sensors of wearable device 110A. As an example and not by way of limitation, the obtaining includes accessing EEG data of the user stored in memory or performing the calculation on the brain-wave data to compute EEG-Excitement, EEG-Q2, etc. by EEG-evaluation module 610 as the brain-wave data is being captured. At step 730, emotion-evaluation system 600 may determine an arousal of the user based on the user's brain-wave activity during the period of time. In particular embodiments. At step 730, emotion-evaluation system 600 may determine an estimate of an emotion of the user during the period of time based on the shift in SVB and emotional state characteristic. Then, the method 700 may terminate.

In particular embodiments, prior to determining the SVB shift, the method 700 may determine synchronize the cardiac-activity data with the brain-wave data, upsample the cardiac-activity data, and then smooth the upsampled cardiac-activity data. Particular embodiments may repeat one or more steps of method 700 of FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates an example method for evaluating emotions of a user, including the particular steps of the method of FIG. 7, this disclosure contemplates any suitable method for evaluating emotions of a user including any suitable steps, which may include all, some, or none of the steps of the method of FIG. 7, where appropriate. Furthermore, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

In particular embodiments, wearable device 110A may be a head-mounted display (HMD) with one or more sensors configured to measure brain-wave activity. In particular embodiments, content or a setting associated with content may be adjusted based on the evaluated emotion of the user. As an example and not by way of limitation, server 140 providing content to the user through a wearable device (e.g., 110A) server 140 may provide the video stream in an interactive way based on the emotion of the user from data captured by wearable devices 110A-B. For example, server 140 may provide a video stream and an input from wearable devices 110A-B may evaluate the emotion of the user to server 140. Server 140 may dynamically serve content to evoke a particular emotion. As an example and not by way of limitation, server 140 may select one or more frames of a video stream that evokes a feeling of relaxation for the user and transmit the selected frames (e.g., cats playing with yarn) for display on wearable device 110A.

As another example, server 140 may transmit a video stream corresponding to scenes of a video game for display on wearable device 110A. Server 140 may evaluate the emotion of the user during game play and adjusting the difficulty level of the game based on the emotion of the user. For example, if the user is expressing frustration during game play, server 140 may transmit game content having a lower difficulty level based on detecting frustration by the user. Conversely, server 140 may transmit game content corresponding to a higher difficulty level based on detecting boredom.

As another example, with regard to virtual-reality (VR) content, server 140 may have content of a particular scene with multiple perspectives. Server 140 may select frames corresponding to a particular perspective that the user experiences excitement. In particular embodiments, server 140 may refrain from selecting frames corresponding to a particular perspective that the user experiences stress or tension. In particular embodiments, server 140 may monitor the emotional state of the user and adjust the content or settings associated with the content based on the real-time evaluation of the emotional state of the user.

In particular embodiments, server 140 may send the user one or more recommendations for additional content based on the evaluated emotions of the user while consuming particular content. For example, server 140 may send a recommendation for similar genres of games (e.g., first-person shooter or social game) based on determining the user was experiencing happiness or excitement while playing a particular game. As another example, server 140 may send a recommendation for a different genre of movies or television shows (e.g., action or sports) based on determining the user was experiencing depression or fatigue while watching a particular movie or television show. An example application is in content rating for evaluating design and impact of various types of contents. For example, the system can be used to determine whether a video game that is intended to be thrilling evokes a feeling of thrill in users. Each type of content or content may have different target emotions to be measured. These target emotions can be referred to as primary and secondary desired emotions for the given content, which may be defined by the metadata associated with the content file. Also, for some content, the user may be willing to provide a self-evaluation of the user's arousal and valence while consuming the content. Emotional energy can be used provide automatic content rating. For example, emotional energy can be computed in accordance with the following:

$$EE = Type \times (Valance^2 + Arousal^2) \quad (1)$$

where EE is the emotional energy, Type=1 for positive emotions and −1 for negative emotions, Valance is the energy associated with the brain-wave data, and Arousal is the energy associated with the cardiac-activity data.

In another example embodiment, emotional energy can be computed in accordance with the following:

$$EE = Type \times (Valance^2 + Arousal^2 + K \times Dominance^2) \quad (2)$$

where EE is the emotional energy, Type=1 for positive emotions and −1 for negative emotions, Valance is the energy associated with the brain-wave data, Arousal is the energy associated with the cardiac-activity data, K is a constant (e.g., less than 0.25), and Dominance is a function of an amount of time a user's gaze is fixed about a target viewing area. In particular embodiments, dominance can be measured in a VR application where dominance increases when the user's gaze is fixed about a target viewing area.

Without the valence and arousal given separately by the user, the quality of the content can be calculated as follows:

$$QC = \Sigma_{i=k}(\text{All instances}[DPW \times LPE] + \Sigma_{i=m} \text{All instances}[DSW \times LSE]) \quad (3)$$

where QC is the quality of the content, DPW is the weight of the desired-primary emotion, LPE is the length of time of the instance of the desired-primary emotion, DSW is the weight of the desired-secondary emotion, LSE is the length of time of the instance of the desired-secondary emotion, k is the number of instances of desired-primary-emotion for particular content, and m number of instances of desired-secondary emotion for particular content. In particular embodiments, this formula can be expanded to include undesired emotions whose weight is negative, and hence such instances will subtract from the total.

In particular embodiments, for a given a set of content, the content rating of a number n different content may be determined by sorting the normalized list of the corresponding n QCs calculated using equation (3) above. The normalization can take into account not just the total length of the content but also the desired goal for how long the given emotion must be generated in the user. As an example and not by way of limitation, a 30 second humorous clip may have a lower QC value than the QC value for a 2 minute humorous clip if the emotion generated were equally intense.

A user's home may include one or more internet-connected devices (e.g., thermostat, lighting, or media server) in a "smart home." In particular embodiments, server 140 may adjust a setting of one or more internet-connected devices based on the emotional state of the user. As an example and not by way of limitation, server 140 may adjust an amount of lighting (e.g., dim) based on detecting that the user is experiencing tension. As another example, server 140 may adjust a thermostat setting (e.g., warmer) based on the detecting the user is continuing to experience tension.

In particular embodiments, a record of the emotional state of the user may be used to determine or verify whether particular treatments are effective. As an example and not by way of limitation, particular courses of treatment may be found to evoke positive or high valance emotions in a user or patient, such that the health practitioner may emphasize these particular courses of treatment over courses of treatment evoking negative emotions. As another example, a user or patient may be diagnosed with deep or severe depression based on a lack of positive emotions experienced by the patient.

In particular embodiments, a camera or other media recording device may be activated at times when the user is experiencing positive emotions. As an example and not by way of limitation, a video camera attached to the user may start recording in response to detecting the user experiencing positive emotions (e.g., elation or excitement).

Figure 8:
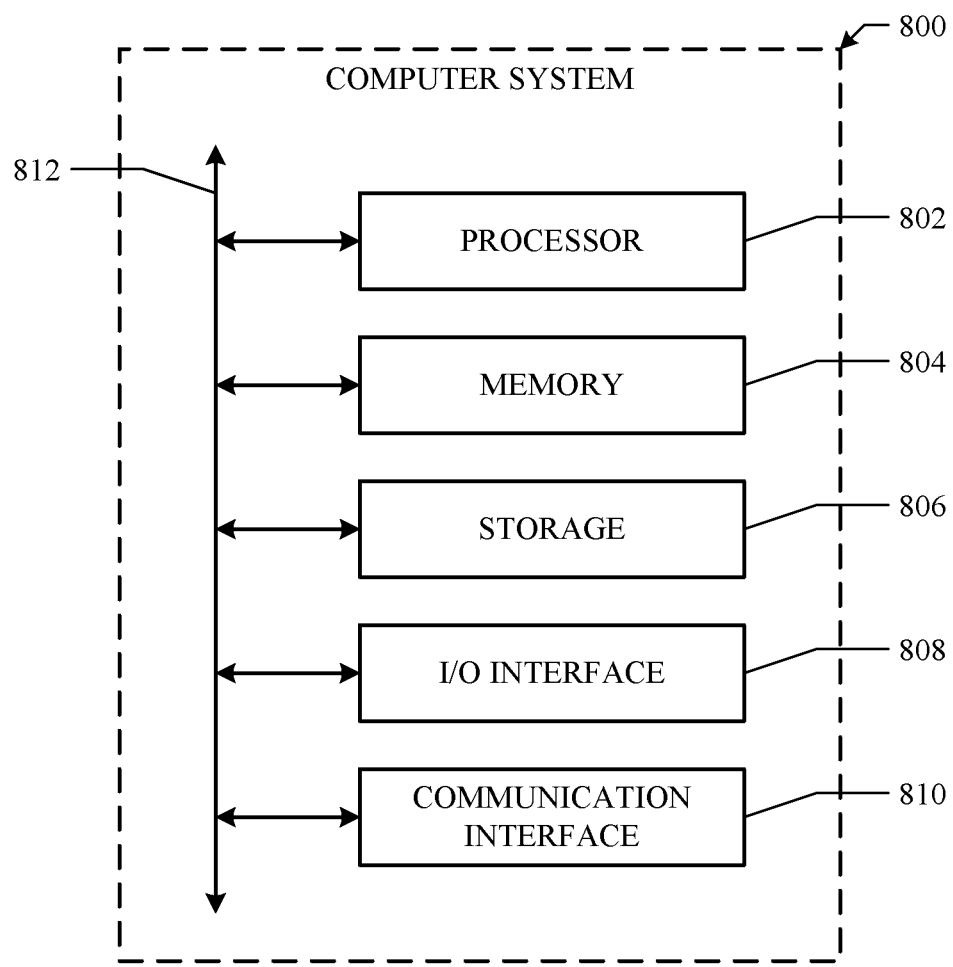
FIG. 8 illustrates an example computer system according to particular embodiments of the invention.

FIG. 8 illustrates an example computer system 800 according to some embodiments of the invention. In particular embodiments, one or more computer systems 800 perform one or more steps of one or more methods described or illustrated herein. In particular embodiments, one or more computer systems 800 provide functionality described or illustrated herein. In particular embodiments, software running on one or more computer systems 800 performs one or more steps of one or more methods described or illustrated herein or provides functionality described or illustrated herein. Particular embodiments include one or more portions of one or more computer systems 800. Herein, reference to a computer system may encompass a computing device, and vice versa, where appropriate. Moreover, reference to a computer system may encompass one or more computer systems, where appropriate.

This disclosure contemplates any suitable number of computer systems 800. This disclosure contemplates computer system 800 taking any suitable physical form. As example and not by way of limitation, computer system 800 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 800 may include one or more computer systems 800; be unitary or distributed; span multiple locations; span multiple machines; span multiple data centers; or reside in a cloud, which may include one or more cloud components in one or more networks. Where appropriate, one or more computer systems 800 may perform without substantial spatial or temporal limitation one or more steps of one or more methods described or illustrated herein. As an example and not by way of limitation, one or more computer systems 800 may perform in real time or in batch mode one or more steps of one or more methods described or illustrated herein. One or more computer systems 800 may perform at different times or at different locations one or more steps of one or more methods described or illustrated herein, where appropriate.

In particular embodiments, computer system 800 includes a processor 802, memory 804, storage 806, an input/output (I/O) interface 808, a communication interface 810, and a bus 812. Although this disclosure describes and illustrates a particular computer system having a particular number of particular components in a particular arrangement, this disclosure contemplates any suitable computer system having any suitable number of any suitable components in any suitable arrangement.

In particular embodiments, processor 802 includes hardware for executing instructions, such as those making up a computer program. As an example and not by way of limitation, to execute instructions, processor 802 may retrieve (or fetch) the instructions from an internal register, an internal cache, memory 804, or storage 806; decode and execute them; and then write one or more results to an internal register, an internal cache, memory 804, or storage 806. In particular embodiments, processor 802 may include one or more internal caches for data, instructions, or addresses. This disclosure contemplates processor 802 including any suitable number of any suitable internal caches, where appropriate. As an example and not by way of limitation, processor 802 may include one or more instruction caches, one or more data caches, and one or more translation lookaside buffers (TLBs). Instructions in the instruction caches may be copies of instructions in memory 804 or storage 806, and the instruction caches may speed up retrieval of those instructions by processor 802. Data in the data caches may be copies of data in memory 804 or storage 806 for instructions executing at processor 802 to operate on; the results of previous instructions executed at processor 802 for access by subsequent instructions executing at processor 802 or for writing to memory 804 or storage 806;

or other suitable data. The data caches may speed up read or write operations by processor 802. The TLBs may speed up virtual-address translation for processor 802. In particular embodiments, processor 802 may include one or more internal registers for data, instructions, or addresses. This disclosure contemplates processor 802 including any suitable number of any suitable internal registers, where appropriate. Where appropriate, processor 802 may include one or more arithmetic logic units (ALUs); be a multi-core processor; or include one or more processors 802. Although this disclosure describes and illustrates a particular processor, this disclosure contemplates any suitable processor.

In particular embodiments, memory 804 includes main memory for storing instructions for processor 802 to execute or data for processor 802 to operate on. As an example and not by way of limitation, computer system 800 may load instructions from storage 806 or another source (such as, for example, another computer system 800) to memory 804. Processor 802 may then load the instructions from memory 804 to an internal register or internal cache. To execute the instructions, processor 802 may retrieve the instructions from the internal register or internal cache and decode them. During or after execution of the instructions, processor 802 may write one or more results (which may be intermediate or final results) to the internal register or internal cache. Processor 802 may then write one or more of those results to memory 804. In particular embodiments, processor 802 executes only instructions in one or more internal registers or internal caches or in memory 804 (as opposed to storage 806 or elsewhere) and operates only on data in one or more internal registers or internal caches or in memory 804 (as opposed to storage 806 or elsewhere). One or more memory buses (which may each include an address bus and a data bus) may couple processor 802 to memory 804. Bus 812 may include one or more memory buses, as described below. In particular embodiments, one or more memory management units (MMUs) reside between processor 802 and memory 804 and facilitate accesses to memory 804 requested by processor 802. In particular embodiments, memory 804 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 804 may include one or more memories 804, where appropriate. Although this disclosure describes and illustrates particular memory, this disclosure contemplates any suitable memory.

In particular embodiments, storage 806 includes mass storage for data or instructions. As an example and not by way of limitation, storage 806 may include a hard disk drive (HDD), a floppy disk drive, flash memory, an optical disc, a magneto-optical disc, magnetic tape, or a Universal Serial Bus (USB) drive or a combination of two or more of these. Storage 806 may include removable or non-removable (or fixed) media, where appropriate. Storage 806 may be internal or external to computer system 800, where appropriate. In particular embodiments, storage 806 is non-volatile, solid-state memory. In particular embodiments, storage 806 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 806 taking any suitable physical form. Storage 806 may include one or more storage control units facilitating communication between processor 802 and storage 806, where appropriate. Where appropriate, storage 806 may include one or more storages 806. Although this disclosure describes and illustrates particular storage, this disclosure contemplates any suitable storage.

In particular embodiments, I/O interface 808 includes hardware, software, or both, providing one or more interfaces for communication between computer system 800 and one or more I/O devices. Computer system 800 may include one or more of these I/O devices, where appropriate. One or more of these I/O devices may enable communication between a person and computer system 800. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 808 for them. Where appropriate, I/O interface 808 may include one or more device or software drivers enabling processor 802 to drive one or more of these I/O devices. I/O interface 808 may include one or more I/O interfaces 808, where appropriate. Although this disclosure describes and illustrates a particular I/O interface, this disclosure contemplates any suitable I/O interface.

In particular embodiments, communication interface 810 includes hardware, software, or both providing one or more interfaces for communication (such as, for example, packet-based communication) between computer system 800 and one or more other computer systems 800 or one or more networks. As an example and not by way of limitation, communication interface 810 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 810 for it. As an example and not by way of limitation, computer system 800 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 800 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 800 may include any suitable communication interface 810 for any of these networks, where appropriate. Communication interface 810 may include one or more communication interfaces 810, where appropriate. Although this disclosure describes and illustrates a particular communication interface, this disclosure contemplates any suitable communication interface.

In particular embodiments, bus 812 includes hardware, software, or both coupling components of computer system 800 to each other. As an example and not by way of limitation, bus 812 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 812 may include one or more buses 812, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. One or more computer-readable non-transitory storage media embodying software that is operable when executed to:
    estimate, based on cardiac-activity data, a shift in sympathovagal balance (SVB) during a period of time, the shift in SVB comprising a shift in a number of data points in a cardiac-activity histogram relative to a center point in a baseline histogram, the center point in the baseline histogram dividing the baseline histogram such that half of the data points in the baseline histogram have a value less than a value of the center point and half of the data points in the baseline histogram have a value greater than the value of the center point;
    obtain an emotional-state characteristic, the emotional-state characteristic being based on brain-wave activity data; and
    determine, based on the SVB shift and the emotional-state characteristic, an estimate of an emotional state of the user during the period of time.

2. The media of claim 1, wherein the software is further operable to determine, based on the cardiac-activity data, a heart rate (HR) or heart-rate variation (HRV) of the user during the period of time; and wherein the estimated emotional state of the user is further based on the HR or HRV during the period time.

3. The media of claim 1, wherein the software is further operable to calculate a covariance between the estimated SVB shift and the emotional-state characteristic.

4. The media of claim 1, wherein the emotional-state characteristic comprises a plurality of emotional states, each of the plurality of emotional states comprising a plurality of specific emotions.

5. The media of claim 1, wherein the brain-wave activity data is stored in memory or measured in real-time.

6. The media of claim 1, wherein the software is further operable to determine one or more features of the brain-wave activity data, and wherein one or more of the features comprise an energy level that is greater than a predefined threshold.

7. The media of claim 1, wherein the software is further operable to compute electroencephalogram short-term excitement (EEG-STE) data based on the brain-wave activity data.

8. The media of claim 1, wherein the software is further operable to:
    identify a first quadrant of a two-dimensional space based on the brain-wave activity of the user; and
    identify a second quadrant of the two-dimensional space based on the estimated shift in SVB, and wherein the first and second quadrant each corresponds to a plurality of candidate emotional states of the user during the period of time.

9. The media of claim 8, wherein the software is further operable to determine whether the first quadrant corresponds to the second quadrant.

10. The media of claim 1, wherein the software is operable to flag the period of time based on the estimated SVB shift and a change in the emotional-state characteristic during the period of time.

11. The media of claim 1, wherein the period of time is longer than a pre-determined threshold amount of time.

12. The media of claim 1, wherein the brain-wave activity is detecting using a head-worn apparatus comprising a plurality of electrodes and a head-mounted display (HMD).

13. The media of claim 1, wherein the software is further operable to calculate an emotional energy that is based on the cardiac-activity data and the brain-wave activity data.

14. The media of claim 13, wherein the software is further operable to determine a rating for content based on the calculated emotional energy.

15. The media of claim 1, wherein the software is further operable to:

receive feedback identifying whether the estimated emotional state of the user correctly identified an emotion of the user during the period of time; and store the feedback in a data structure accessible by one or more machine learning algorithms.

16. The media of claim 1, wherein the software is further operable to:

synchronize the cardiac-activity data with the brain-wave activity data;

upsample the cardiac-activity data or the brain-wave activity data; and smooth the cardiac-activity data or the brain-wave activity data.

17. A method comprising:

estimating, based on cardiac-activity data, a shift in sympathovagal balance (SVB) during a period of time, the shift in SVB comprising a shift in a number of data points in a cardiac-activity histogram relative to a center point in a baseline histogram, the center point in the baseline histogram dividing the baseline histogram such that half of the data points in the baseline histogram have a value less than a value of the center point and half of the data points in the baseline histogram have a value greater than the value of the center point;

obtaining an emotional-state characteristic, the emotional-state characteristic being based on brain-wave activity data; and determining, based on the SVB shift and the emotional-state characteristic, an estimate of an emotional state of the user during the period of time.

18. The method of claim 17, further comprising determining, based on the cardiac-activity data, a heart rate (HR) or heart-rate variation (HRV) of the user during the period of time; and wherein the estimated emotional state of the user is further based on the HR or HRV during the period time.

19. A system comprising:

one or more processors; and a non-transitory memory coupled to the processors comprising instructions executable by the processors, the processors being operable when executing the instructions to:

estimate, based on cardiac-activity data, a shift in sympathovagal balance (SVB) during a period of time, the shift in SVB comprising a shift in a number of data points in a cardiac-activity histogram relative to a center point in a baseline histogram, the center point in the baseline histogram dividing the baseline histogram such that half of the data points in the baseline histogram have a value less than a value of the center point and half of the data points in the baseline histogram have a value greater than the value of the center point;

obtain an emotional-state characteristic, the emotional-state characteristic being based on brain-wave activity data; and determine, based on the SVB shift and the emotional-state characteristic, an estimate of an emotional state of the user during the period of time.

20. The system of claim 19, wherein the processors are further operable to determine, based on the cardiac-activity data, a heart rate (HR) or heart-rate variation (HRV) of the user during the period of time; and wherein the estimated emotional state of the user is further based on the HR or HRV during the period time.

\* \* \* \* \*